(12) United States Patent
Hollis et al.

(10) Patent No.: US 11,266,451 B2
(45) Date of Patent: Mar. 8, 2022

(54) MODULAR BONE IMPLANT DEVICES AND MEANS OF INSERTION

(71) Applicant: CrossRoads Extremity Systems, LLC, Memphis, TN (US)

(72) Inventors: Chad Hollis, Collierville, TN (US); Vernon Hartdegen, Collierville, TN (US); Daniel Sayger, Southaven, MS (US); Daniel J. Triplett, Providence, UT (US); Gregory C. Berlet, Westerville, OH (US); Christopher F. Hyer, Columbus, OH (US)

(73) Assignee: CrossRoads Extremity Systems, LLC, Memphis, TN (US)

( * ) Notice: Subject to any disclaimer, the term of this patent is extended or adjusted under 35 U.S.C. 154(b) by 38 days.

(21) Appl. No.: 16/820,332

(22) Filed: Mar. 16, 2020

(65) Prior Publication Data

US 2020/0305940 A1 Oct. 1, 2020

Related U.S. Application Data

(60) Provisional application No. 62/820,764, filed on Mar. 19, 2019.

(51) Int. Cl.
*A61B 17/80* (2006.01)
*A61B 17/064* (2006.01)
(Continued)

(52) U.S. Cl.
CPC ...... *A61B 17/8061* (2013.01); *A61B 17/0642* (2013.01); *A61B 17/068* (2013.01);
(Continued)

(58) Field of Classification Search
CPC ............ A61B 17/8061; A61B 17/0642; A61B 17/1775; A61B 17/8615; A61B 17/068;
(Continued)

(56) References Cited

U.S. PATENT DOCUMENTS 5,885,299 A * 3/1999 Winslow ............... A61F 2/4637
606/99
6,830,571 B2 12/2004 Lenke et al.
(Continued)

OTHER PUBLICATIONS

International Search Report and Written Opinion dated Jul. 29, 2020 in application No. PCT/US20/23004.

*Primary Examiner* — Marcela I. Shirsat
(74) *Attorney, Agent, or Firm* — Knobbe, Martens, Olson & Bear, LLP

(57) ABSTRACT

A modular bone fixation implant includes a center post having exterior bone engaging features and configured to be implanted within a bone. The center post includes an aperture at an outer end of the center post. One or more interchangeable modular components may be placed within the bone and anchored to the aperture of the center post. Interchangeable modular components may include staples, bone plates, and spacers, each having at least a first end including a post engaging arm sized and shaped to seat within an interlocking feature of the aperture. A locking screw is provided to anchor all components to the center post when the interchangeable modular components have been placed.

18 Claims, 26 Drawing Sheets

(51) Int. Cl.
*A61B 17/86* (2006.01)
*A61B 17/56* (2006.01)
*A61F 2/46* (2006.01)
*A61B 17/068* (2006.01)
*A61F 2/44* (2006.01)
*A61B 17/17* (2006.01)

(52) U.S. Cl.
CPC ....... *A61B 17/0682* (2013.01); *A61B 17/1775* (2016.11); *A61B 17/809* (2013.01); *A61B 17/864* (2013.01); *A61B 17/8615* (2013.01); *A61B 2017/0645* (2013.01); *A61B 2017/0647* (2013.01); *A61B 2017/564* (2013.01); *A61F 2/4425* (2013.01); *A61F 2/4637* (2013.01)

(58) Field of Classification Search
CPC ............... A61B 17/809; A61B 17/864; A61B 17/0682; A61B 2017/564; A61B 2017/0645; A61B 2017/0647; A61F 2/4637; A61F 2/4425
USPC .......................................................... 606/71
See application file for complete search history.

(56) References Cited

U.S. PATENT DOCUMENTS

| | | |
|---|---|---|
| 10,195,045 B2 | 2/2019 | Muller et al. |
| 10,292,713 B2 | 5/2019 | Fallin et al. |
| 2004/0034353 A1* | 2/2004 | Michelson ......... A61B 17/0642 623/13.14 |
| 2007/0239278 A1* | 10/2007 | Heinz ................... A61F 2/4425 623/17.15 |
| 2007/0270833 A1 | 11/2007 | Bonutti |
| 2012/0209331 A1 | 4/2012 | Michelson |
| 2017/0281157 A1 | 10/2017 | Hartdegen et al. |

* cited by examiner

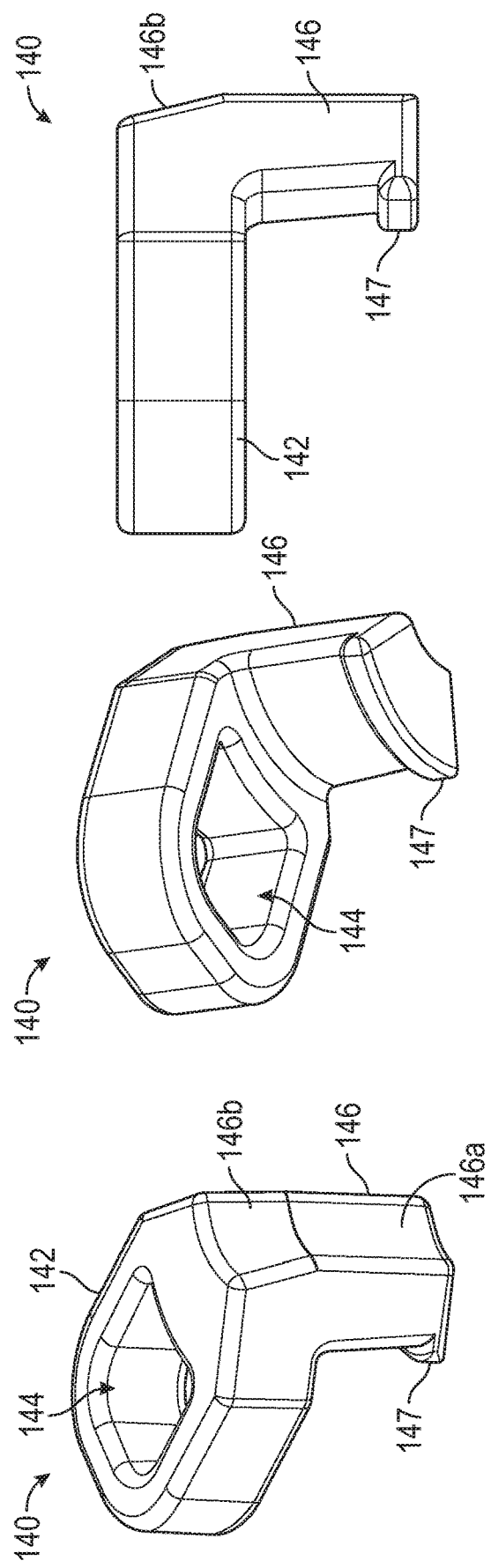

_MODULAR BONE IMPLANT DEVICES AND MEANS OF INSERTION_

CROSS-REFERENCE TO RELATED APPLICATIONS

This application claims the benefit of U.S. Provisional Application Ser. No. 62/820,764, filed Mar. 19, 2019, entitled "MODULAR BONE IMPLANT DEVICES AND MEANS OF INSERTION," which is incorporated by reference herein in its entirety and for all purposes.

FIELD

The present disclosure relates to medical devices and more particularly to bone fixation devices and systems.

BACKGROUND

Implantable devices such as staples, bone screws, bone plates, and the like, are typically used in surgical bone fixation procedures. Many existing implants such as staples may only allow for fixation between two points, or between a limited number and fixed arrangement of points. Other existing implants, such as bone plates or the like, may provide for fixation at a larger number of points in a fixed orientation due to the rigidity of constituent materials. Such implants may be undesirable for internal fixation in locations such as the midfoot, other portions of the foot, and/or other locations in which several relatively small bones are to be fixed or where variation in skeletal geometry between patients is common.

SUMMARY

Example embodiments described herein have innovative features, no single one of which is indispensable or solely responsible for their desirable attributes. Without limiting the scope of the claims, some of the advantageous features will now be summarized.

In one embodiment, a modular bone fixation system comprises a center post defining a central axis, at least one secondary component, and a locking screw. The center post has an exterior and an interior, the exterior comprising an outward facing surface, the interior comprising: an aperture disposed about the central axis on a proximal end of the center post, the aperture configured to receive one or more post engaging members; and a channel extending along the central axis from the aperture toward a distal end of the center post opposite the proximal end, at least a portion of the channel comprising internal screw threads. The at least one secondary component comprises one or more of: a bone plate component comprising a plate having a first plate end and a second plate end, the first plate end comprising a first post engaging member configured to engage the aperture of the center post, the second plate end comprising a fastener receiving member configured to receive a fastener therethrough; and a staple component comprising a bridge having a first bridge end and a second bridge end, the first bridge end contiguous with a second post engaging member configured to engage the aperture of the center post, the second bridge end contiguous with a bone engaging member, wherein the staple component is deformable between a first configuration and a second configuration. The locking screw comprises screw threads configured to engage with the internal screw threads of the center post and a head configured to retain the first post engaging member and the second post engaging member within the aperture when the screw threads of the locking screw are engaged with the internal screw threads of the center post.

The aperture of the center post can comprise an interlocking feature in a sidewall of the aperture, and the first post engaging member or the second post engaging member can comprise a lateral extension configured to seat within the interlocking feature. The aperture of the center post can be a circular aperture and can be configured to receive the first or second post engaging member at any of a plurality of angular locations about the aperture. The modular bone fixation implant can further comprise a spacer component, the spacer component comprising a post engaging member configured to engage the aperture of the center post, and a spacer body configured to extend laterally away from the center post when the post engaging member is disposed within the aperture. The spacer body can comprise an aperture. The center post can further comprise a plurality of driver engagement features disposed radially about an exterior of the aperture, the driver engagement features configured to receive one or more post head engagement features of a driver such that the driver can exert a rotational force on the center post about the central axis. The bone engaging features of the center post can comprise one or more screw threads. The bone engaging features of the center post can be self-tapping screw threads. The outward facing surface of the center post can comprise one or more bone engaging features thereon. The bone engaging member of the staple component can comprise one or more bone engaging features disposed thereon. The one or more bone engaging features of the staple component can comprise ridges oriented to prevent withdrawal of the bone engaging member from a bone. The fastener can be a bone screw.

In another embodiment, a bone fixation system comprises an implant and an inserter connectable to the implant. The implant comprises a bridge, a bone engaging member integrally formed with the bridge at a first end, and a second-implant engaging member integrally formed with the bridge at a second end opposite the first end, wherein the implant is deformable between a first configuration and a second configuration. When the inserter is connected to the implant, the inserter is actuatable to deform the implant between the first configuration and the second configuration, and the implant is fully seatable in a final position in which the bone engaging member abuts an interior portion of bone and the second-implant engaging member is engaged with a second implant. When the implant is fully seated in the final position against the bone and the inserter is disconnected from the implant, the implant applies force to the bone in at least a first direction.

The second-implant engaging member can extend perpendicular to the bridge and can comprise a lateral extension configured to engage an interlocking feature in an aperture of the second implant. The bridge can comprise a first extension extending longitudinally from the bridge at the first end, the first extension configured to engage a first retaining member of the inserter; and a plurality of second extensions extending laterally from the bridge proximate the second end, the plurality of second extensions configured to engage second retaining members of the inserter. The inserter can comprise a plunger movably coupled within the inserter and extendable toward an intermediate portion of the bridge between the first end and the second end to deform the implant between the first configuration and the second configuration. The inserter can be removable from the implant when the plunger is retracted away from the intermediate portion of the bridge by translating the inserter along a direction substantially parallel to the bridge toward the first end of the bridge.

In another embodiment, a modular implant kit comprises a center post configured to be implanted within bone, wherein the center post defines a central axis of a bone fixation implant, a plurality of interchangeable secondary components, and a locking screw. The plurality of interchangeable secondary components are selected from: one or more staple components comprising a first end configured to be anchored to the center post and a second end configured to engage bone at a location disposed radially outward from the center post; one or more bone plate components comprising a first end configured to be anchored to the center post and a second end configured to receive a bone fastener therethrough to engage bone at a location disposed radially outward from the center post; and one or more spacer components comprising a first end configured to be anchored to the center post. The locking screw is configured to engage internal screw threads of the center post to lock individual first ends of one or more of the plurality of interchangeable secondary components to the center post.

The modular implant kit can further comprise an inserter configured to facilitate insertion of the one or more staple components. The modular implant kit can further comprise a drill guide coupleable to the center post, wherein, when the drill guide is coupled to the center post, the drill guide is rotatable about the central axis to define a plurality of drilling locations for placing the one or more staple components. The modular implant kit can further comprise one or more bone screws sized and shaped to couple to the second end of the one or more bone plate components. The modular implant kit can further comprise a post driver coupleable to the center post to facilitate application of a rotational force about the central axis to drive the center post into the tissue. The post driver can comprise a longitudinal coupling feature configured to engage the internal screw threads of the center post to longitudinally fix the center post relative to the post driver, and one or more rotational coupling features configured to interlock with a head of the center post to rotationally fix the center post relative to the post driver.

In another embodiment, a method for internal fixation of one or more bones using a modular bone implant comprises implanting a center post at a first location within the one or more bones, the center post defining a central axis, the center post comprising an exterior and an interior, the exterior comprising an outward facing surface, the interior comprising: an aperture disposed about the central axis on a proximal end of the center post, the aperture configured to receive one or more post engaging members; and a channel extending along the central axis from the aperture toward a distal end of the center post opposite the proximal end at least a portion of the channel comprising internal screw threads. The method further comprises implanting at least one secondary implant into a second location within the one or more bones, the at least one secondary implant comprising a post engaging member disposed at a first end of the secondary implant and a second end configured to be coupled to the one or more bones at the second location, the post engaging member configured to engage the aperture of the center post; and securing the at least one secondary implant to the center post by inserting a locking screw into the channel such that one or more screw threads of the locking screw engage the internal screw threads of the channel and a head of the locking screw retains the post engaging member of the at least one secondary implant within the aperture.

The at least one secondary implant can comprise a bone plate component having a fastener receiving member disposed at the second end, the fastener receiving member configured to receive a fastener therethrough for securing the second end to the one or more bones at the second location. Implanting can comprise inserting a bone screw through the fastener receiving member and into the one or more bones to secure the second end to the one or more bones at the second location. The at least one secondary implant can comprise a staple component having a bone engaging member disposed at the second end. The staple component can be deformable between a first configuration and a second configuration, and implanting the at least one secondary implant can comprise retaining the staple component in the first configuration within an inserter, placing the staple component such that the post engaging member of the staple component is at least partially within the aperture of the center post and the bone engaging member is at least partially disposed within the one or more bones at the second location, and releasing the staple component from the inserter such that the staple component assumes the second configuration. The method can further comprise coupling a spacer to the center post prior to inserting the locking screw, the coupling comprising placing a post engaging member of a spacer component within the aperture. At least two secondary implants can be implanted at locations spaced angularly about the central axis.

BRIEF DESCRIPTION OF THE DRAWINGS

Aspects and advantages of the embodiments provided herein are described with reference to the following detailed description in conjunction with the accompanying drawings. Throughout the drawings, reference numbers may be re-used to indicate correspondence between referenced elements. The drawings are provided to illustrate example embodiments described herein and are not intended to limit the scope of the disclosure.

FIGS. 8A-8C depict an example spacer component of a modular bone implant device.

FIGS. 9A and 9B depict an example locking screw component of a modular bone implant device.

DETAILED DESCRIPTION

The following description is directed to certain implementations for the purpose of describing the innovative aspects of this disclosure. However, a person having ordinary skill in the art will readily recognize that the teachings herein can be applied in a multitude of different ways.

Generally described, the systems, devices, and methods described herein provide a modular bone implant device that can be customized to suit individual implant placement locations. The modular bone implant device may be provided in a kit and can include a plurality of optional and/or interchangeable implant components that may be selected, positioned, and secured at the time of placement. Accordingly, the modular bone implant device may allow a surgeon to perform a procedure such as internal fixation or osteosynthesis more effectively than would be possible with conventional bone implants that are not modular or otherwise customizable.

The embodiments described herein can be manufactured from a number of different materials or combinations of materials. Nitinol, for example, possess material properties, such as shape memory and/or super elasticity that may provide the inherent properties to allow an embodiment to have multiple configurations with or without an external mechanical manipulation. Stainless steel and/or titanium also have desirable material properties for the embodiments described herein. Stainless steel and/or titanium may not possess shape memory or super elasticity, but may possess the mechanical properties for embodiments that may benefit from mechanical manipulation to achieve multiple configurations. Still other materials such as PEEK or other polymers may also possess material properties beneficial for the embodiment described herein. A combination of materials may also be preferred. For example, a combination of nitinol and titanium (e.g., a nitinol plate with titanium screws) may be the materials of choice for some embodiments. Those skilled in the art are aware of the typical materials and combinations of materials applicable to the current technology.

Figure 1A:
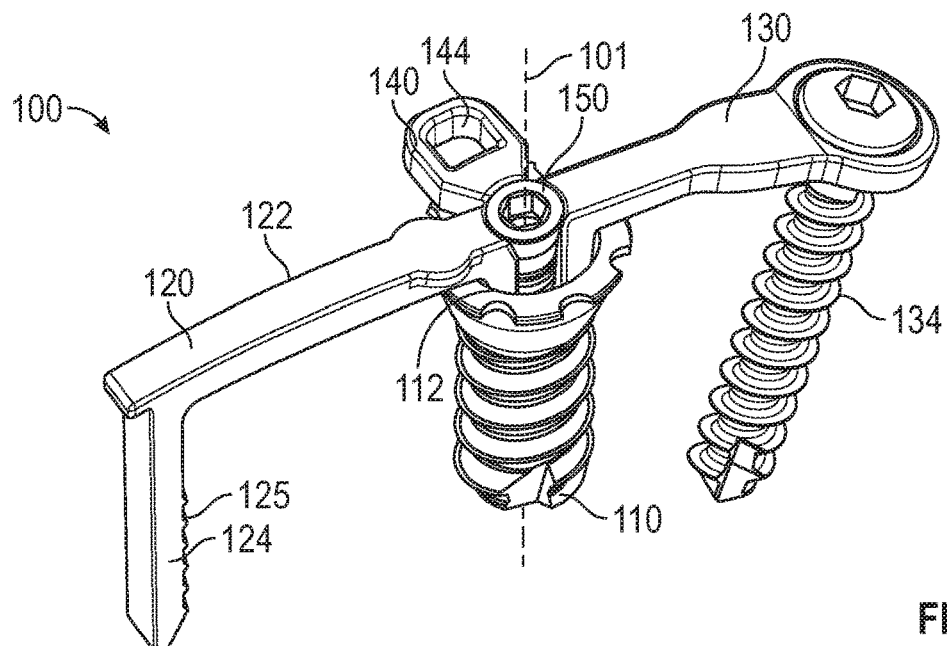
FIGS. 1A-1E depict a modular bone implant device including an example combination of modular components.
Figure 1B:
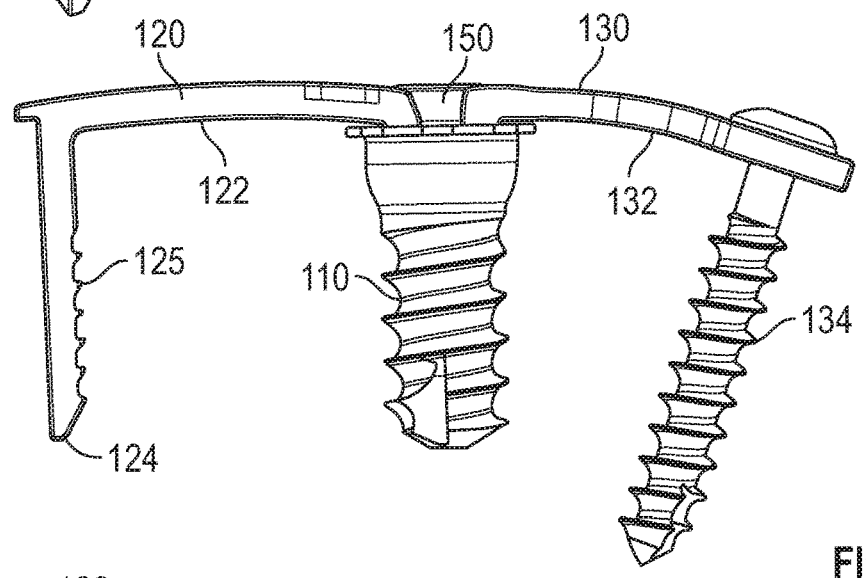
Figure 1C:
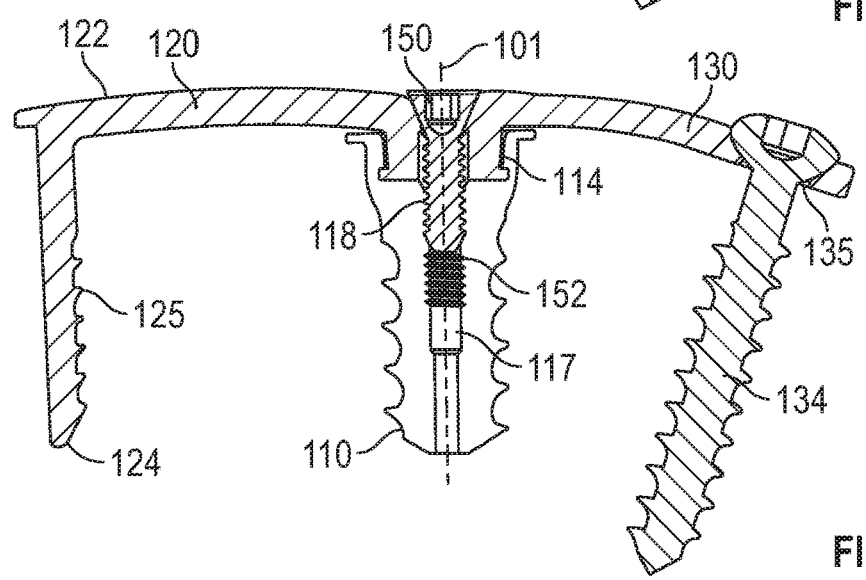
Figure 1D:
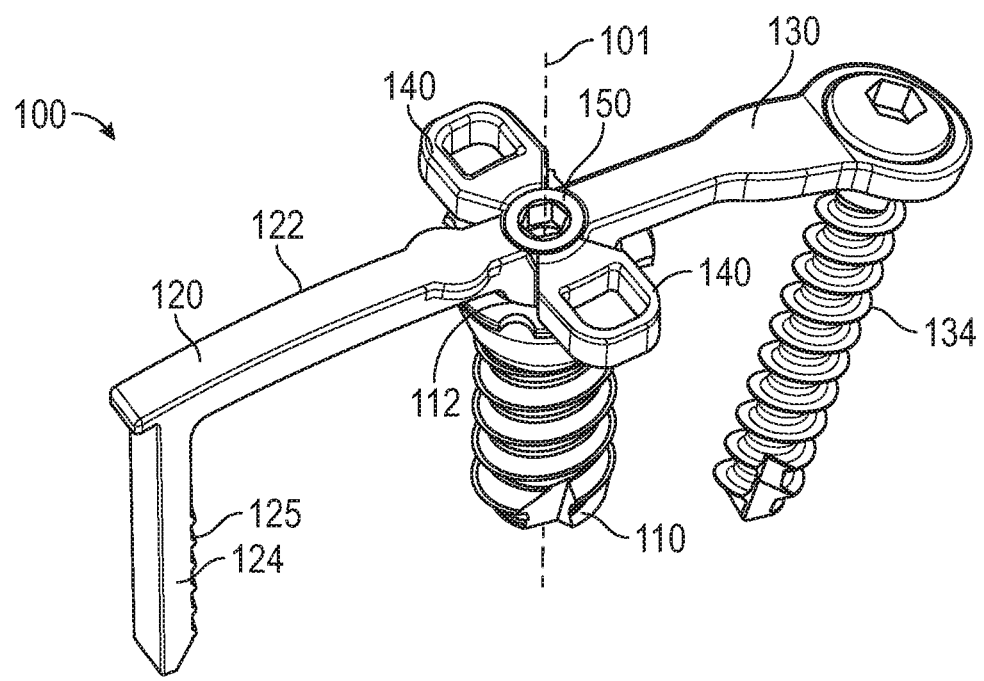
Figure 1E:
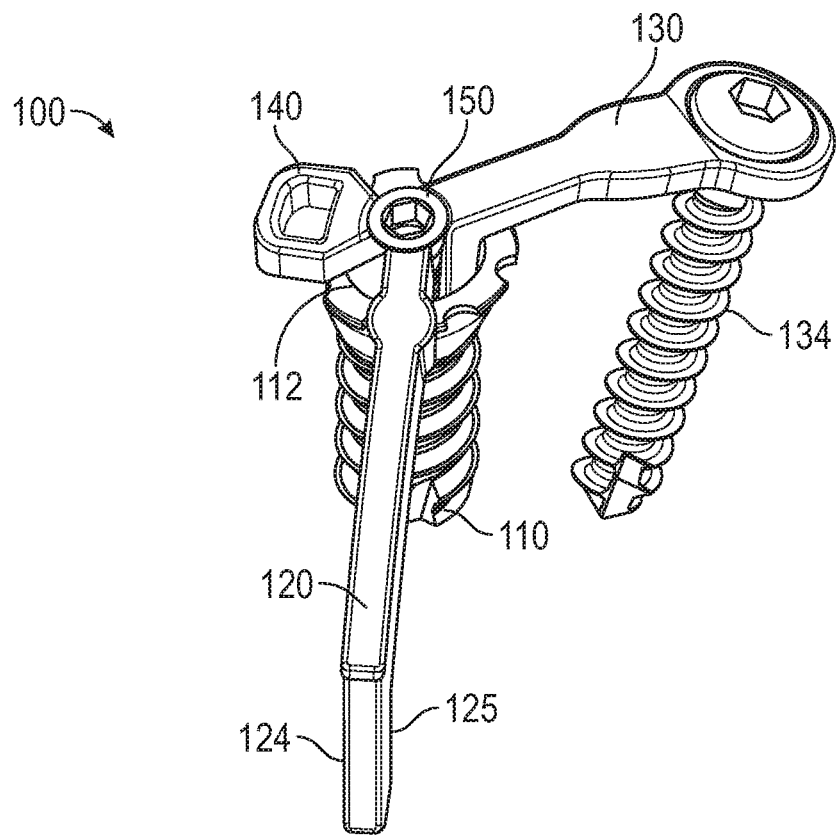

FIGS. 1A-1E illustrate example embodiments of an assembled implant 100 including various modular components described herein. FIG. 1A is a top perspective view of the implant 100 in a first configuration including a staple component 120, a bone plate component 130, and a spacer component 140. FIG. 1B is a side view of the implant 100 in the first configuration, and FIG. 1C is a cross-sectional view illustrating internal components of the implant 100 in the first configuration. FIGS. 1D and 1E depict the implant 100 in alternative configurations including different combinations or positioning of components relative to the first configuration.

The implant 100 includes a center post 110 defining a central axis 101 of the implant 100. The center post 110 has a threaded exterior configured to anchor the center post 110 within a bone. An upper portion of the center post 110 includes an aperture 112. Other modular components, such as one or more staple components 120, bone plate components 130, and/or spacer components 140, may be coupled to the center post 110 by engaging an arm of the component within the aperture 112 of the center post 110. The staple components 120, bone plate components 130, and/or spacer components 140 are secured to the center post at fixed or variable angular locations about the center post 110 by a locking screw 150. For example, the angular locations of the staple components 120, bone plate components 130, and/or spacer components 140 may be adjustable while the locking screw 150 is absent or loosely inserted, and may be fixed by inserting and fully tightening the locking screw 150. The locking screw 150 includes threads 152 that engage with internal threads 118 of a channel 117 extending through the shaft of the center post 110. In some embodiments, the center post 110 may be seated within the bone before the other components of the implant 100. The center post 110 is described in greater detail with reference to FIGS. 2A-2E.

The staple component 120 includes a bridge 122 extending outward from the center post 110 and a bone engaging member 124 extending from the bridge 122 at an end of the bridge 122 distal from the center post 110. Bone engaging features 125 on an inward-facing side of the bone engaging member 124 are provided to prevent the bone engaging member 124 from withdrawing from a bone after the staple component 120 is placed. The staple component 120 engages with the aperture 112 of the center post 110 at the opposite end of the bridge 122. The staple component 120 is described in greater detail with reference to FIGS. 4A and 4B.

The bone plate component 130 includes a plate 132 extending outward from the center post 110. An aperture 135 extends through the plate 132 at an end of the plate 132 distal from the center post 110. The aperture 135 is configured to receive a bone screw 134 to anchor the bone plate component 130 to a bone. The bone plate component 130 is described in greater detail with reference to FIGS. 7A-7G.

The spacer component 140 is provided to occupy a portion of the aperture 112 of the center post 110 and does not directly engage with the bone. One or more spacer components 140 may be utilized in the implant 100 as desired to provide stability for the other components. In some embodiments, the spacer component 140 includes an aperture 144 that may serve as a connection point for other structures. For example, a tendon, ligament, or other connective tissue may be secured relative to a spacer component 140. The spacer component 140 is described in greater detail with reference to FIGS. 8A-8C.

FIGS. 1D and 1E illustrate alternative configurations of components of the implant 100. The example configuration of FIG. 1D includes the same set of components as the configuration of FIGS. 1A-1C. However, in the configuration of FIG. 1D, the staple component 120, the bone plate component 130, and the spacer component 140 are spaced angularly at approximately uniform intervals about the central axis 101. In the configuration of FIG. 1E, the implant 100 includes two spacer components 140 disposed on opposite sides of the center post 110 between the staple component 120 and the bone plate component 130.

It will be understood that various other combinations and/or arrangements of the components described herein may equally be implemented without departing from the spirit or scope of the present disclosure. For example, the implant 100 may be packaged as an implant kit including one or more center posts 110, staple components 120, bone plate components 130, spacer components 140, and locking screws 150. Accordingly, any combination of one, two, three, four, five, six, or more of staple components 120, bone plate components 130, and/or spacer components 140 may be secured to a single center post 110 as appropriate for a particular implant location. For example, some applications may require an implant 100 comprising two or more staple components 120, two or more bone plate components 130, and/or two or more spacer components 140 coupled to a center post 110.

Figure 2A:
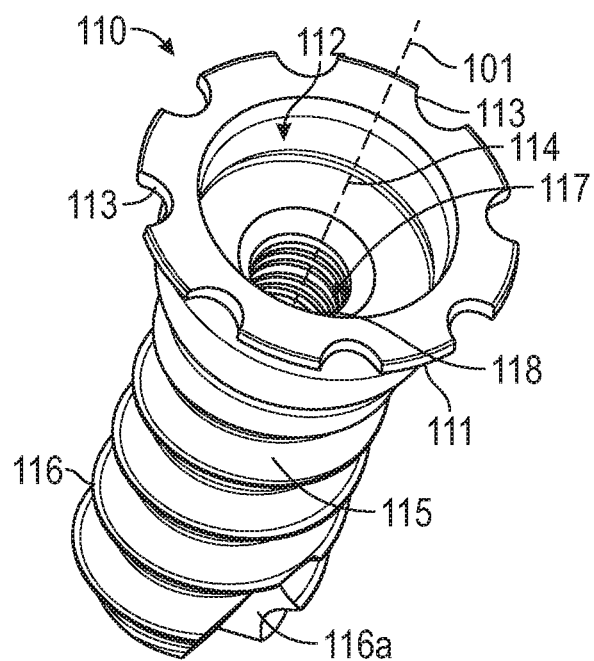
FIGS. 2A-2E depict an example center post component of a modular bone implant device.
Figure 2B:
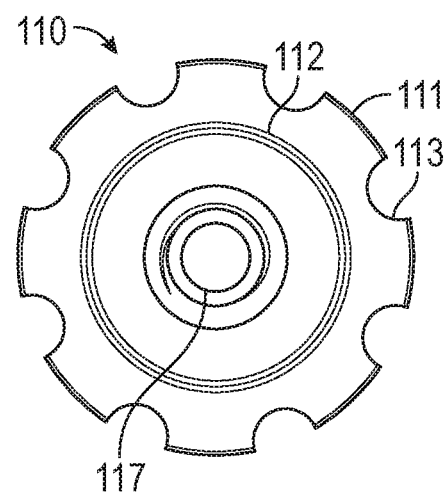
Figure 2C:
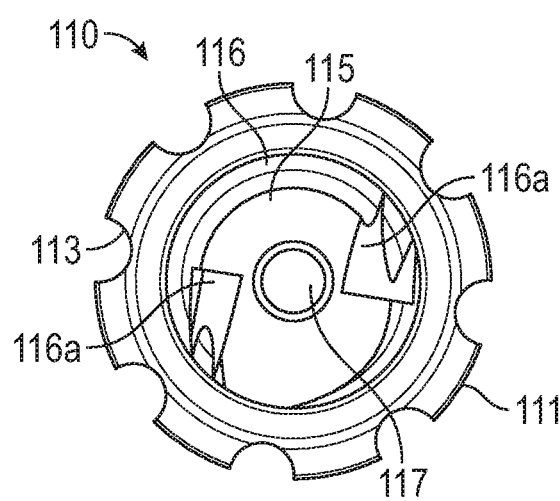
Figure 2D:
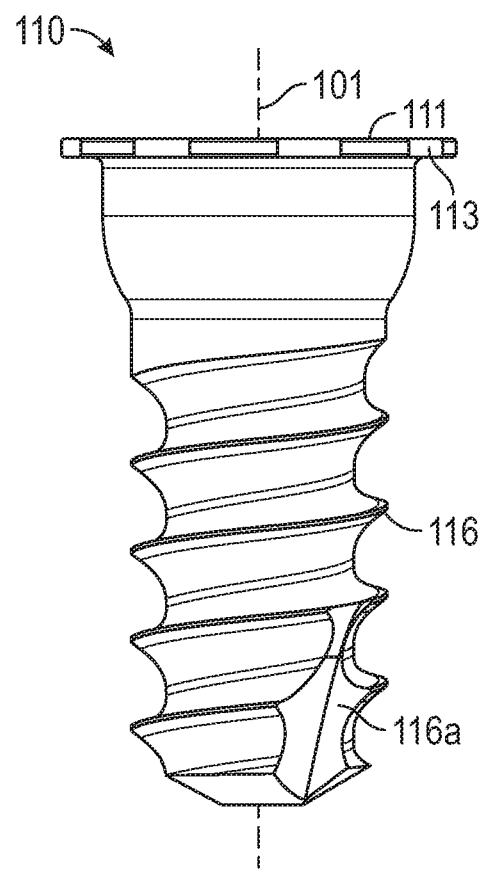
Figure 2E:
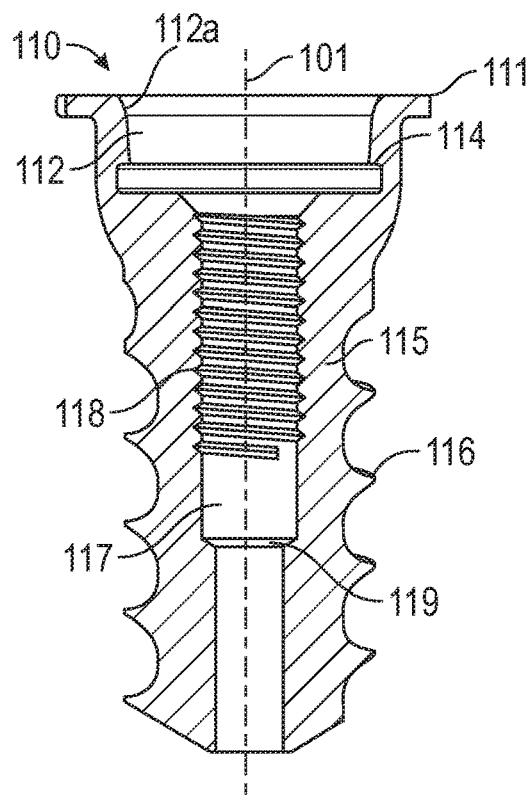

FIGS. 2A-2E depict a center post 110 consistent with the implant 100 of FIGS. 1A-1E. FIG. 2A is a top perspective view of the center post 110. FIGS. 2B and 2C are top and bottom views, respectively, of the center post 110 at locations along the central axis 101. FIG. 2D is a side view of the center post 110, and FIG. 2E is a cross-sectional view taken about the central axis 101 illustrating internal features of the center post 110. In some embodiments, the center post 110 may comprise a single integrally formed component.

The center post 110 includes a head 111 configured to be disposed at or near the surface of a bone in which the center post 110 is placed. In some applications, the head 111 may be countersunk such that the top of the head 111 is approximately flush with the surface of the bone. The head 111 includes driver engagement features 113 located at regular intervals about the circumference of the head 111.

The head 111 of the center post 110 surrounds the aperture 112 to which other components of the implant 100 can be attached. As shown in FIGS. 2A and 2E, an interlocking feature such as an undercut 114 is located at a lower portion of the aperture 112. The undercut 114 may accommodate lateral extensions of post engaging members of the various other components of the implant 100 to prevent vertical motion of the other components after assembly. For example, the cross-sectional view of FIG. 1C illustrates the seating of lateral extensions within the undercut 114. In addition, the interior-facing side surface 112a of the aperture 112 may be tapered such that the aperture 112 is narrower at the bottom near the undercut 114 and wider at the top near the head 111. Tapering of the aperture 112 may allow for a deeper undercut 114 without widening the exterior dimension of the center post 110. Tapering of the aperture 112 may additionally provide a counterforce to axial force generated by tightening the locking screw 150, clamping any modular components such as staple components 120, bone plate components 130, or spacer components 140, to prevent axial or rotational movement of the modular components.

The center post 110 further includes a shaft 115 integrally formed with the head 111. The exterior of the shaft 115 includes bone engagement features 116. The bone engagement features 116 may be screw threads consistent with a bone screw. In some embodiments, the bone engagement features 116 further include flutes 116a extending along a portion of the shaft 115. Flutes 116a may permit the center post 110 to function as a self-tapping bone screw to facilitate placement within the bone. At least a portion of the shaft 115 is hollow and surrounds a channel 117 having internal threads 118 angled and pitched to engage with the locking screw 150 of FIGS. 1A-1C. The channel 117 is contiguous with the aperture 112 at an upper end of the channel 117. In some embodiments, the channel 117 extends through the entire length of the shaft 115 and may include a notch 119 defining a maximum entry depth for the locking screw 150. Embodiments in which the channel 117 extends through the entirety of the shaft 115 may function as cannulated screws, and may be insertable over a guide wire.

Figure 3A:
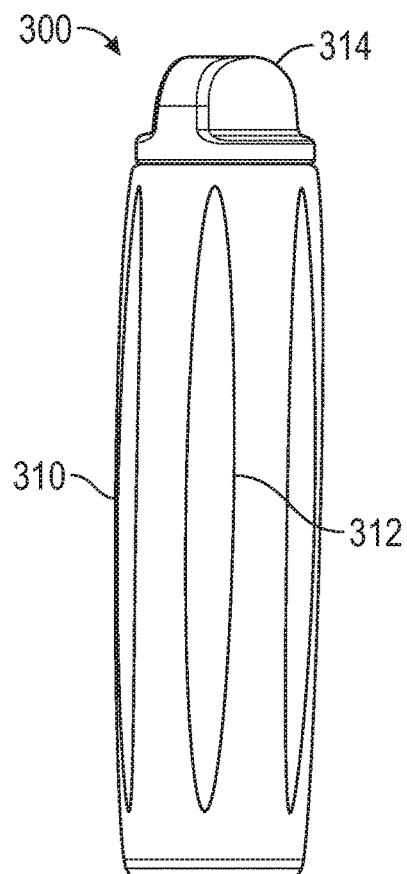
FIGS. 3A and 3B depict an example post driver configured to be used with the center post of FIGS. 2A-2E.
Figure 3B:
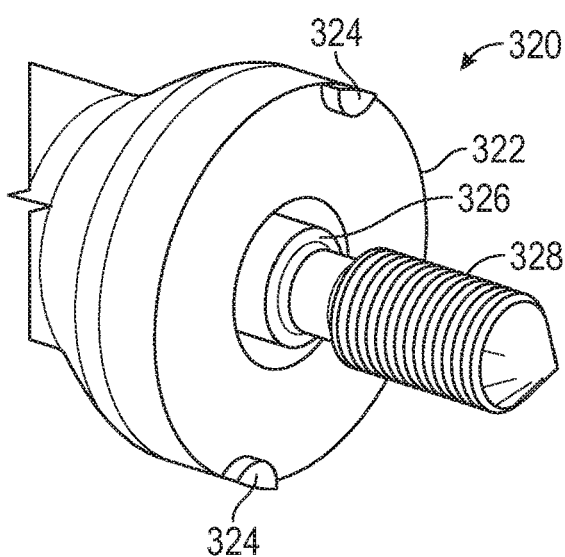

FIGS. 3A and 3B depict an example post driver 300 configured for insertion of the center post 110 of FIGS. 2A-2E. The post driver 300 includes a handle 310 and a post engagement section 320 sized and shaped to removably engage the center post 110. FIG. 3B is an enlarged perspective view illustrating components of the post engagement section 320. The handle 310 may include one or more ergonomic features 312 such as indentations, ridges, or the like to facilitate gripping of the handle 310 by a user. The post engagement section 320 includes a post abutting surface 322, post head engagement features 324, and a central shaft 326 having one or more post channel engagement features 328 disposed thereon.

The post abutting surface 322 is generally planar and is configured to abut the top surface of the head 111 of a center post 110 as illustrated in FIGS. 2A-2E. The post head engagement features 324 have a complementary size and shape corresponding to the size and shape of the driver engagement features 113 of the center post 110. When the post abutting surface 322 is placed against the head 111 of the center post 110 with the post head engagement features 324 engaged within opposing driver engagement features 113, the center post 110 is rotationally fixed about the central axis 101 relative to the post driver 300. Although the example post driver 300 of FIGS. 3A and 3B includes two post head engagement features 324, some embodiments may include three or more post head engagement features 324. For the example center post 110 of FIGS. 2A-2E, a compatible post driver 300 may have up to eight post head engagement features 324 spaced about the circumference of the post head abutting surface 322.

The central shaft 326 is a linear member extending through a central portion of the handle 310 of the post driver 300. The central shaft 326 is rotatable and longitudinally translatable relative to the handle 310. A central shaft grip 314 is fixed to the central shaft 326 and is disposed at the opposite end of the handle 310 such that the central shaft grip 314 can be used to manipulate the central shaft 326 relative to and independent of the handle 310. The post channel engagement features 328 are disposed at the end of the central shaft 326 opposite the central shaft grip 314. In some embodiments, the post channel engagement features 328 comprise one or more screw threads having a pitch and angle consistent with the pitch and angle of the threads of the locking screw 150 (FIGS. 1A-1C) so that the post channel engagement features 328 can engage the internal threads 118 of the center post 110 to longitudinally fix a center post 110 coupled to the post driver 300.

With combined reference to FIGS. 2A-3B, an example method of placing a center post 110 using the post driver 300 will now be described. To couple the center post 110 to the post driver 300, the post channel engagement features 328 are inserted through the aperture 112 into the channel 117 of the center post 110. The central shaft grip 314 is then rotated (e.g., clockwise) about the central axis 101 relative to the center post 110 until the threads of the post channel engagement features 328 are at least partially engaged within the internal threads 118 of the center post 110. The handle 310 may then be moved toward the center post 110 and rotated as necessary such that the head 111 of the center post 110 abuts the post abutting surface 322 and the post head engagement features 324 are seated within the driver engagement features 113 of the center post 110. With the center post 110 rotationally fixed to the handle 310, the central shaft grip 314 is then rotated further until the central shaft grip 314 abuts the handle 310, fixing the center post 110 both longitudinally and rotationally to the post driver 300. The shaft 115 of the center post 110 is placed against a bone (e.g., at the opening of a pre-drilled pilot hole) and the handle 310 is rotated while pressure is applied along the central axis 101 to drive the center post 110 into the bone. When the center post 110 is fully inserted (e.g., the head 111 lies flush with the outer surface of the bone), the post driver 300 is removed from the center post 110 by rotating the central shaft grip 314 (e.g., counterclockwise) to disengage the threads of the post channel engagement features 328 from the internal threads 118 of the center post 110. While the post driver 300 is removed from the center post 110, the handle 310 may be held in a fixed position such that the post head engagement features 324 prevent the rotational disengagement motion of the central shaft 326 from rotating the entire center post 110 and backing the center post 110 out of its intended position within the bone.

Figure 4A:
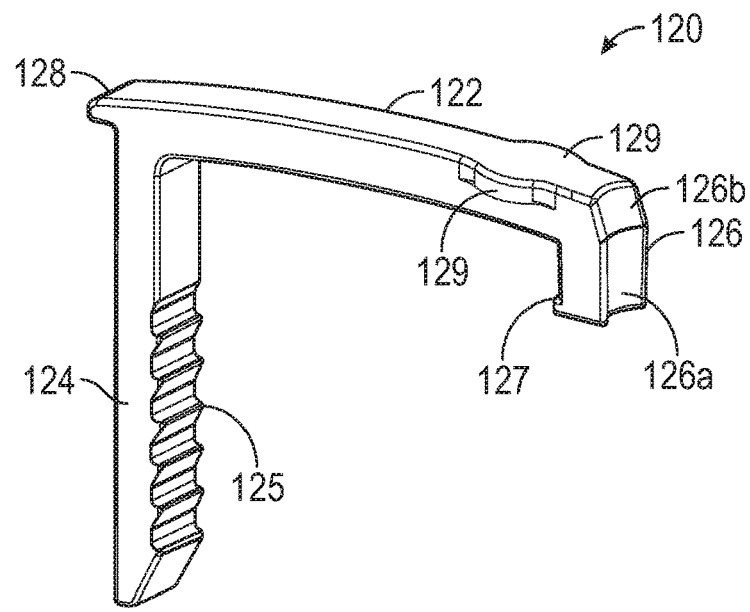
FIGS. 4A and 4B depict an example staple component of a modular bone implant device.
Figure 4B:
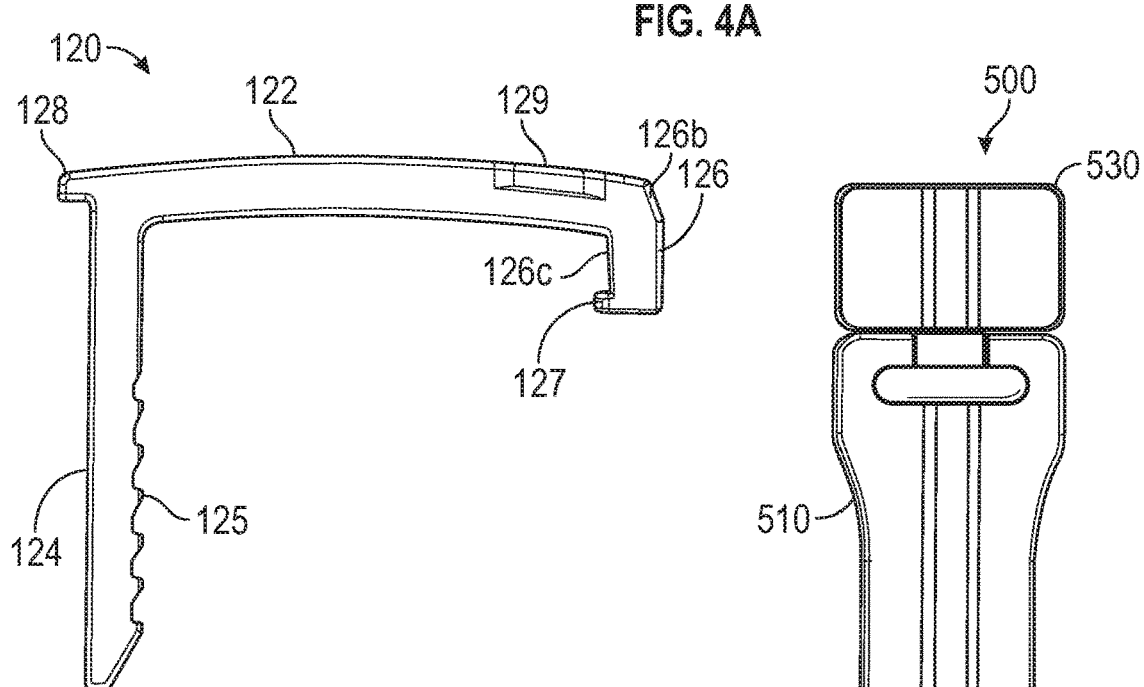

FIGS. 4A and 4B depict a staple component 120 consistent with the implant 100 of FIGS. 1A-1E. The staple component 120 includes a bridge 122, a bone engaging member 124 (for example, a leg) disposed at a first end of the bridge 122, and a post engaging member 126 disposed at a second end of the bridge 122 opposite the bone engaging member 124. In some embodiments, the staple component 120 may comprise a single integrally formed component such that the bone engaging member 124 and the post engaging member 126 are integral to the bridge 122. In some embodiments, the staple component 120 is formed of a shape-memory alloy, such as nitinol.

The bone engaging member 124 includes bone engaging features 125 that improve bone purchase and/or pull out strength of the staple component 120 from bone or soft tissue. In some embodiments, the bridge 122 has a curve or arc such that the bone engaging member 124 is biased inward toward the central axis 101 (FIG. 1A), further improving bone purchase and/or pull out strength of the staple component 120. In some embodiments, the bridge 122 may be resilient such that the bridge 122 can be bent into a linear configuration for insertion, and released to bias toward the curved configuration when the bone engaging member 124 has been seated within the bone. In some embodiments, the bone engaging member 124 is substantially perpendicular to the adjacent portion of the bridge 122. When the bridge 122 is in its relaxed curve shape prior to insertion, the bone engaging member 124 forms an angle relative to the center of the bridge 122. In some embodiments, when the bridge 122 is deformed into a substantially linear configuration and the bone engaging member 124 has been seated within the bone and the deformed bridge 122 has been released, the bridge 122 remains deformed due to the presence of bone between the bone engaging member 124 and the center post 110, such that a compressive force between the bone engaging member 125 and the center post 110 is created.

The post engaging member 126 includes a lateral extension 127 sized to seat within the undercut 114 of the aperture 112 of the center post 110 of FIGS. 2A-2E. The post engaging member 126 may further include a curved axial surface 126a and a bevel 126b shaped to conform to complementary contours of the locking screw 150. In addition, the post engaging member 126 may include a tapered surface 126c opposite the axial surface 126a shaped to match the taper of the side surface 112a of the aperture 112 of the center post 110. Accordingly, seating the post engaging member 126 within the aperture 112 and securing a locking screw 150 within the channel 117 of the center post 110 may rigidly secure the staple component 120 in a fixed position relative to the center post 110.

Figure 5A:
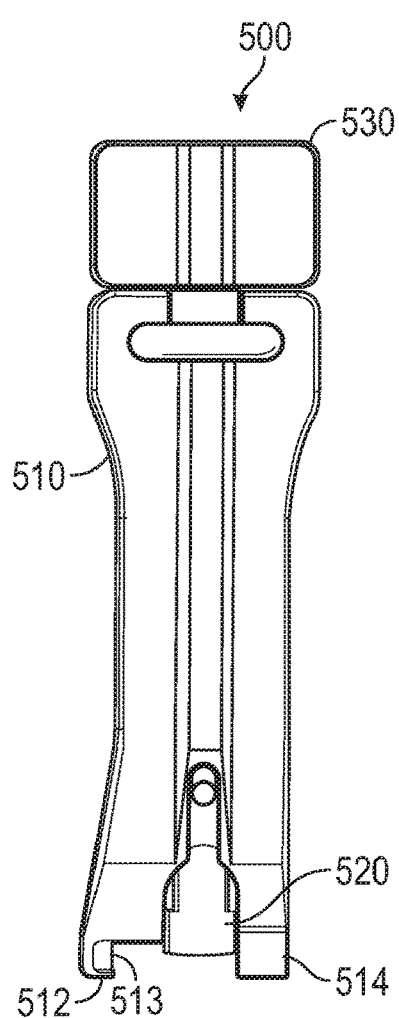
FIGS. 5A-5D depict an example inserter configured to be used with the staple of FIGS. 4A and 4B.
Figure 5D:
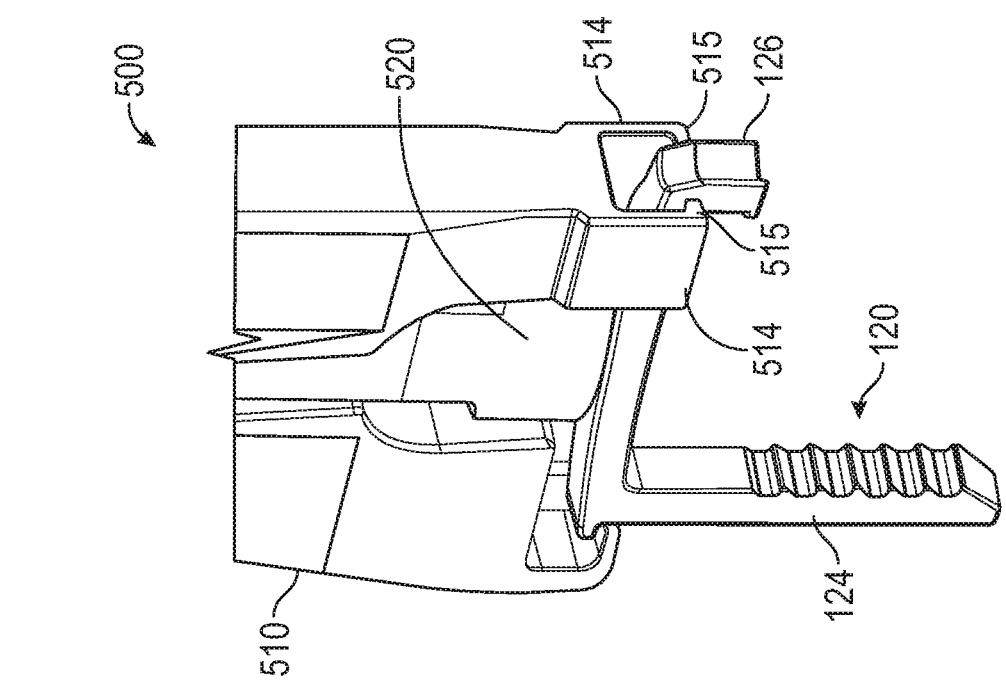
Figure 5C:
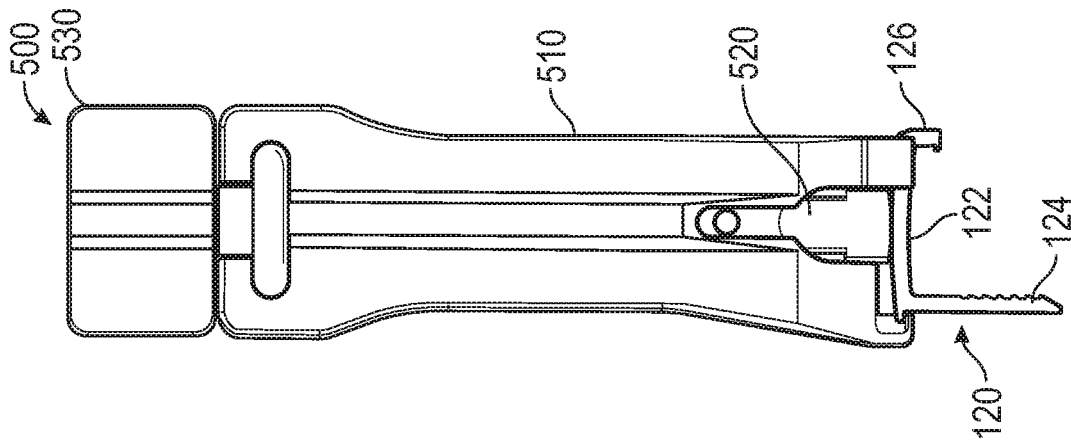
Figure 5B:
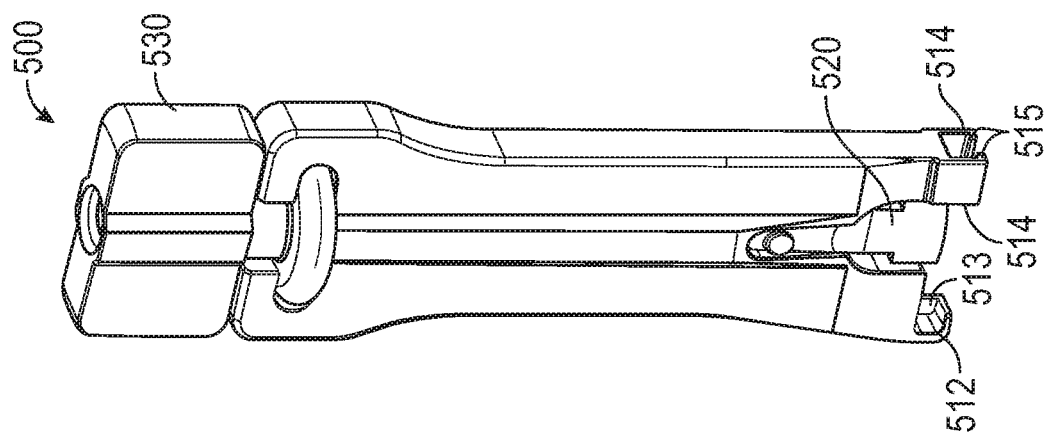

The staple component 120 further includes an end extension 128 extending from the end of bridge 122 adjacent to the bone engaging member 124, and lateral extensions 129 extending laterally from the bridge 122 adjacent to the post engaging member 126, that may serve as connecting means for connecting to an inserter. FIGS. 5A-5D depict an example inserter 500 compatible with the staple component 120 of FIGS. 4A and 4B. FIGS. 5A and 5B depict the inserter 500 in an empty configuration; FIGS. 5C and 5D depict the inserter 500 with a staple component 120 retained therein. FIG. 5D is an enlarged perspective view illustrating the retention of the staple component 120 within the inserter 500.

The inserter 500 includes an inserter body 510, a plunger 520, and a plunger adjustment grip 530. The plunger adjustment grip 530 is rotatable relative to the inserter body 510 to move the plunger 520 longitudinally relative to the inserter body 510. Rotating the plunger adjustment grip 530 in a first direction (e.g., clockwise) causes the plunger 520 to move away from the plunger adjustment grip 530 to secure and/or compress a staple component 120. Rotating the plunger adjustment grip 530 in a second direction (e.g., counterclockwise) causes the plunger 520 to move toward the plunger adjustment grip 530 to release a staple component 120.

The inserter body 510 is configured to retain the staple component 120 and may further serve as a handle for use during placement of the staple component 120. As shown in FIGS. 5C and 5D, a retaining member 512 at one distal end corner of the inserter body 510 includes an extension 513 forming a shelf that may abut a lower surface of the end extension 128 of the staple component 120. Retaining members 514 at the opposite distal end corner of the inserter body 510 include lateral shelfs 515 that may abut lower surfaces of the lateral extensions 129 of the staple component 120. Advantageously, retaining the staple component 120 at opposing ends of the bridge 122 allows the plunger 520 to interact with a central portion of the bridge 122 straighten the bridge 122 (e.g., by continuing to move downward after coming into contact with the bridge 122).

The staple component 120 is preferably placed after a hole has been drilled in the target bone to receive the bone engaging member 124. FIGS. 6A-6D depict a drill guide 600 that facilitates drilling of a hole in a suitable location for placement of the staple component 120. The drill guide 600 includes a center post engaging section 610, a drill location section 620, and a spacing member 630 disposed between the center post engaging section 610 and the drill location section 620. Although the spacing member 630 is depicted as a linear member, in some embodiments the spacing member 630 may have a contoured shape or may be flexible in order to accommodate and/or wrap onto the bone. The drill guide 600 may be a single integrally formed component and may comprise a metal, a plastic, or other suitable material.

Figure 6C:
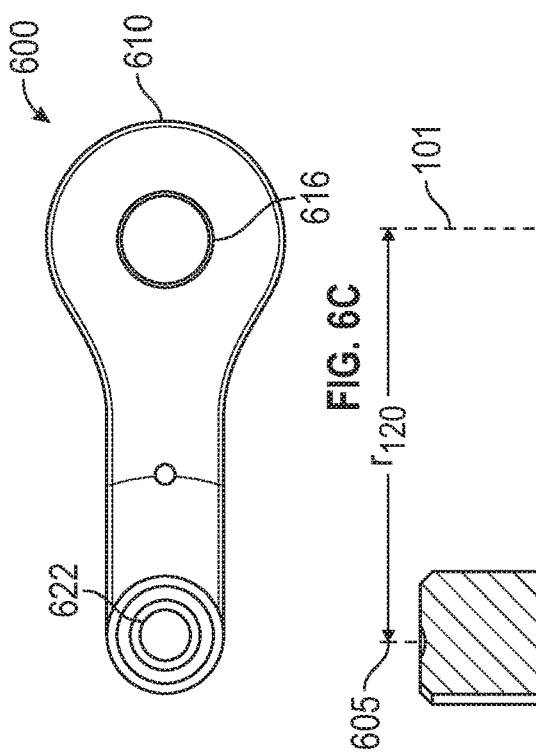
FIGS. 6A-6D depict an example drill guide configured to be used with the staple of FIGS. 4A and 4B.
Figure 6D:
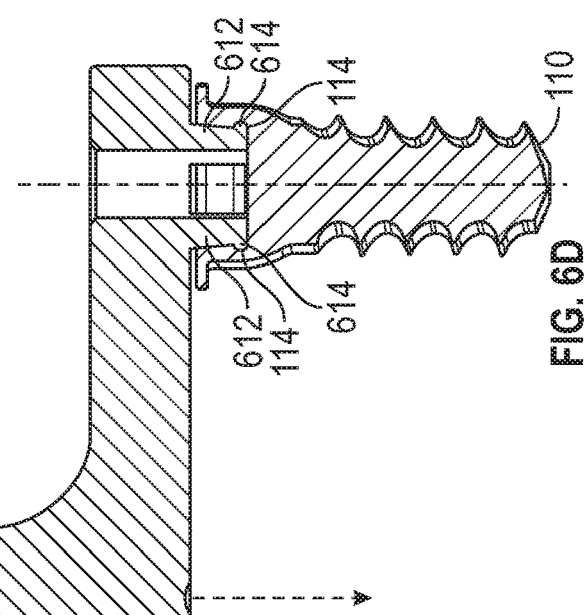
Figure 6A:
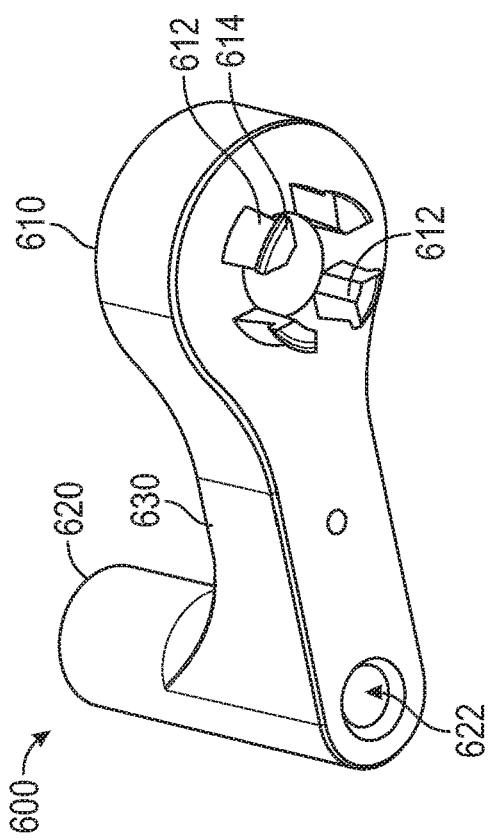
Figure 6B:
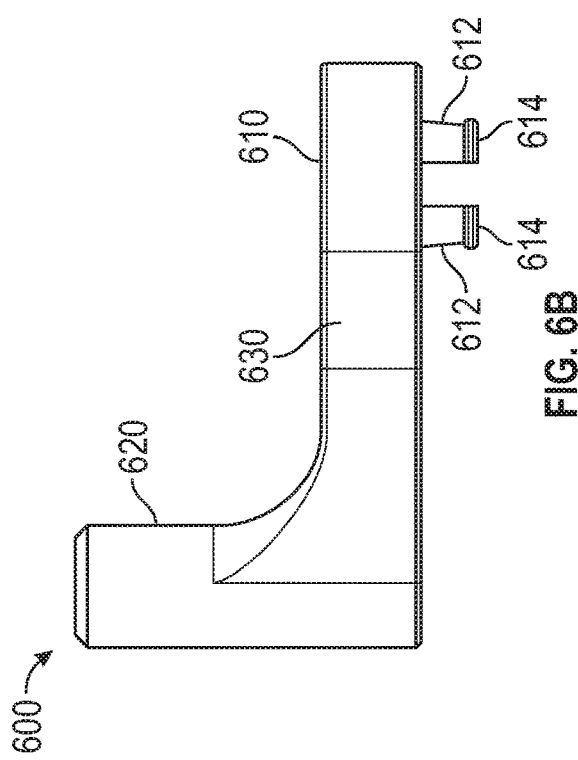

The center post engaging section 610 includes post engaging members 612 and lateral extensions 614 disposed about an aperture 616. The post engaging members 612 are sized and located to seat within the aperture 112 of the center post 110. The lateral extensions 614 extend from the ends of the post engaging members 612 to seat within the undercut 114 of the aperture 112. In some embodiments, the drill guide 600 may comprise a plastic, a metal, or other suitable material to facilitate removably snap fitting the post engaging members 612 and lateral extensions 614 within the aperture 112 and undercut 114. FIG. 6D is a cross-sectional view illustrating the connection between the drill guide 600 and a center post 110.

The drill location section 620 includes an aperture 622 that facilitates selection of a drilling location. In various embodiments, the aperture 622 may accommodate a drill bit or guide wire, or may be used to mark a drill location and removed before drilling or placing a guide wire. The aperture 622 is held at a fixed distance $r_{120}$ relative to the center of the center post engaging section 610 by the spacing section 630. When the post engaging members 612 are seated within the aperture 112 with the lateral extensions 614 disposed within the undercut 114, the drill guide 600 may be freely rotatable about the central axis 101 of the center post 110 such that the fixed radial distance $r_{120}$ between the center post engaging section 610 and the aperture 622 defines a circular set of possible drilling locations suitable for the staple component 120.

With combined reference to FIGS. 4A-6D, an example method of placing a staple component 120 with the drill guide 600 and the inserter 500 will now be described. After a center post 110 has been seated within a bone and the post driver 300 has been removed, the drill guide 600 is coupled to the center post 110 by placing the post engaging members 612 within the aperture 112 such that the lateral extensions 614 are seated within the undercut 114. Using the aperture 622 as a guide, a drilling location is selected and a hole is drilled in the bone at a distance $r_{120}$ from the central axis 101. The drill guide 600 is removed from the center post 110. The staple component 120 is placed into the inserter 500 in the configuration shown in FIGS. 5C and 5D, and the plunger adjustment grip 530 is rotated to compress the bridge 122 of the staple component 120 such that the leg 124 is approximately parallel to the central axis 101 of the central post 110. The staple component 120 may then be inserted by consecutively or simultaneously placing the bone engaging member 124 into the drilled hole in the bone and placing the post engaging member 126 into the aperture 112 of the center post 110 such that the lateral extension 127 of the post engaging member 126 is seated within the undercut 114. The plunger adjustment grip 530 is then rotated in an opposite direction to decompress the bridge 122, allowing the staple component 120 to return towards its biased configuration, thereby providing a compressive force between the bone engaging member 125 and the center post 110. This compressive force can maintain compression across a bone fracture during bone remodeling. The inserter 500 can then be removed from the staple component 120 by translating the inserter 500 radially outward from the central axis 101 such that the retaining member 512 releases the end extension 128 of the staple component 120 and the retaining members 514 release the lateral extensions 129 of the staple component 120.

Figure 7A:
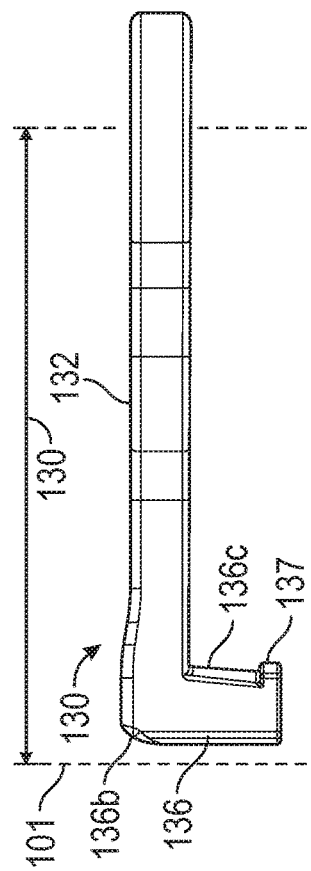
FIGS. 7A-7G depict an example bone plate component and bone screw of a modular bone implant device.
Figure 7B:
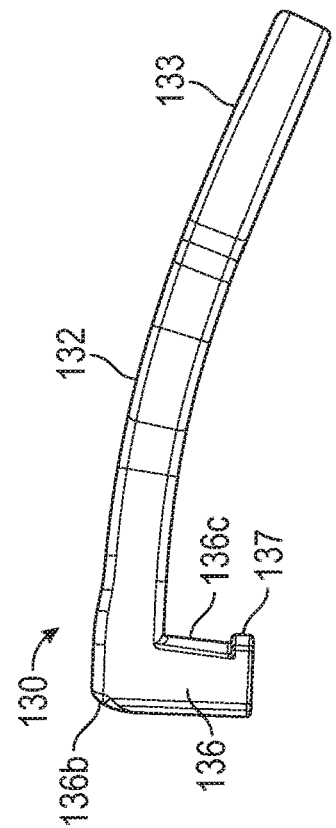
Figure 7C:
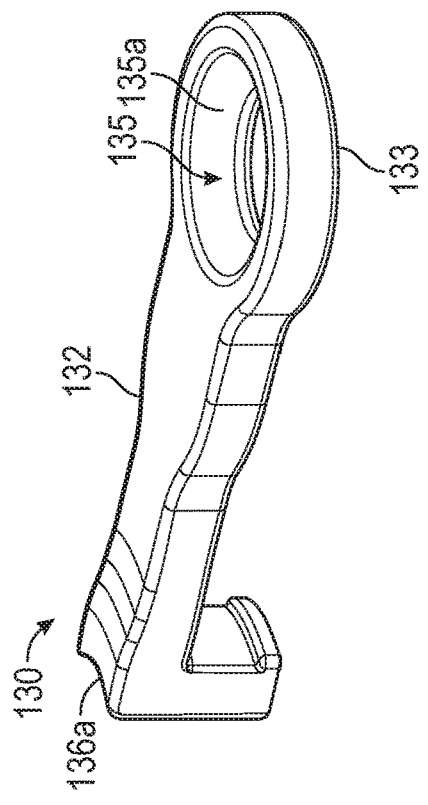
Figure 7D:
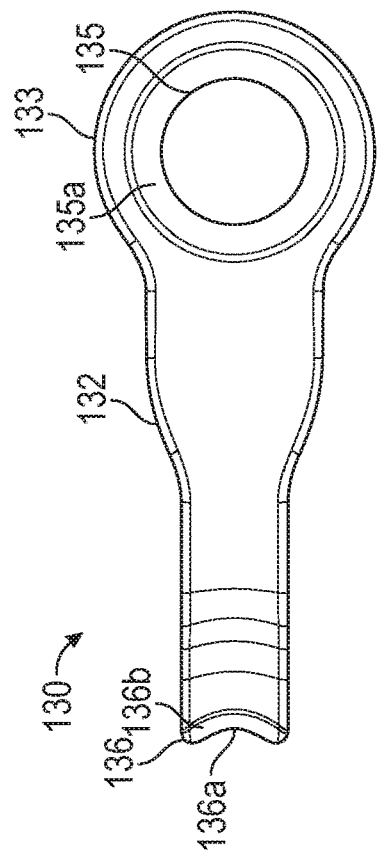
Figure 7G:
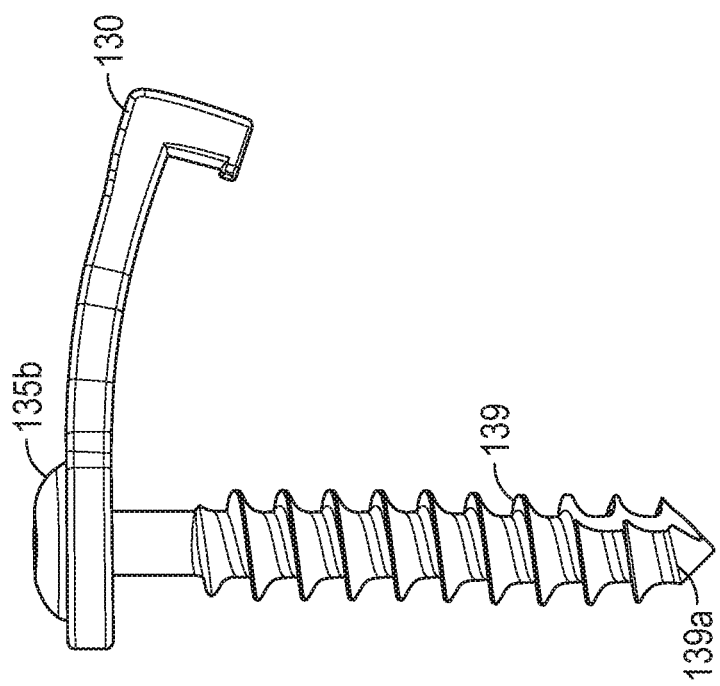
Figure 7F:
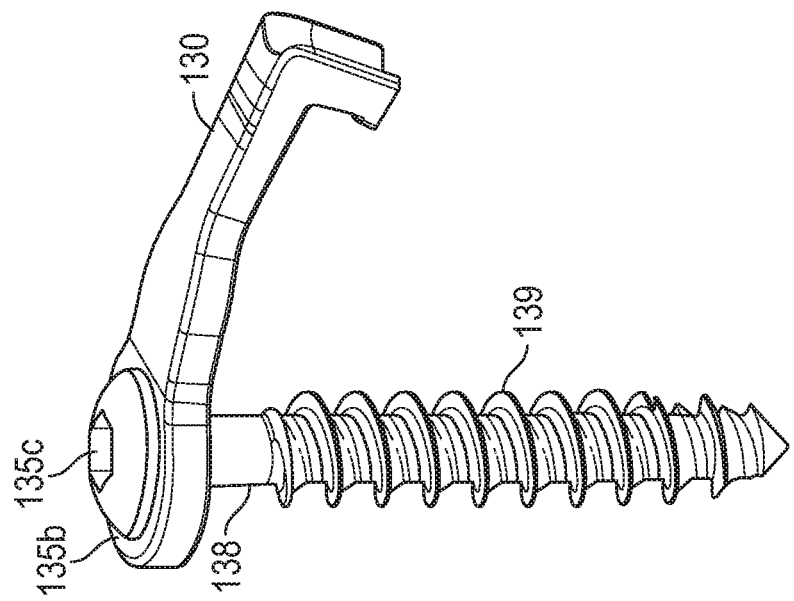
Figure 7E:
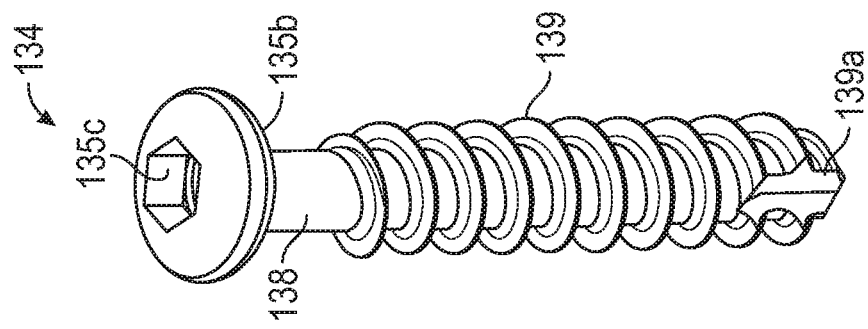

FIGS. 7A-7G depict a bone plate component 130 consistent with the implant 100 of FIGS. 1A-1E. The bone plate component 130 includes a plate 132, a bone screw engaging member 133 disposed at a first end of the plate 132 and including an aperture 135 for receiving a bone screw 134, and a post engaging member 136 disposed at a second end of the plate 132 opposite the bone screw engaging member 133. In some embodiments, the bone plate component 130 may comprise a single integrally formed component such that the bone screw engaging member 133 and the post engaging member 136 are integral to the plate 132. FIGS. 7A-7D depict the bone plate component 130, FIG. 7E depicts an example bone screw 134 compatible with the bone plate component 130, and FIGS. 7F and 7G depict the example bone screw 134 coupled to the bone plate component 130.

The plate 132 defines a radial distance $r_{130}$ between the central axis 101 of the implant 100 and a bone screw entry location defined by the location of the aperture 135. In some embodiments of an implant kit, the kit may include a plurality of bone plate components 130 having differently sized plates 132 such that a plurality of optional radial distances $r_{130}$ are provided. The plate 132 may be bendable as shown in FIG. 7D, for example, to allow the bone screw engaging member 133 to abut the bone to which the bone screw 134 will be inserted. In some embodiments, the plate 132 is formed of a shape-memory alloy, such as nitinol.

The bone screw engaging member 133 includes an aperture 135 sized and shaped to receive a corresponding bone screw 134 for anchoring the distal end of the bone plate component 130 to a bone. An annular surface 135a of the bone screw engaging member 133 surrounds the aperture 135 and is shaped to provide a complementary surface to a head 135b of the bone screw 134.

The post engaging member 136 includes a lateral extension 137 sized to seat within the undercut 114 of the aperture 112 of the center post 110 of FIGS. 2A-2E. The post engaging member 136 may further include a curved axial surface 136a and a bevel 136b shaped to conform to complementary contours of the locking screw 150. In addition, the post engaging member 136 may include a tapered surface 136c opposite the axial surface 136a shaped to match the taper of the side surface 112a of the aperture 112 of the center post 110. Accordingly, seating the post engaging member 136 within the aperture 112 and securing a locking screw 150 within the channel 117 of the center post 110 may rigidly secure the bone screw component 130 in a fixed position relative to the center post 110.

The bone screw 134 includes a head 135b and a shaft 138. The shaft 138 includes bone engagement features 139. The bone engagement features 139 may be screw threads and in some embodiments may include flutes 139a extending along a portion of the shaft 138. The flutes 139a may permit the bone screw 134 to be a self-tapping bone screw to facilitate placement within the bone. The head 135b includes a recess 135c shaped to receive a driver. Although the bone screw 134 of FIGS. 7E-7G includes a hexagonal recess 135c, the recess 135c may equally be implemented as a slotted, Phillips, or any other screw drive shape. It will be appreciated that any suitable bone fastener other than bone screw 134 may be used.

FIGS. 8A-8C depict a spacer component 140 consistent with the implant 100 of FIGS. 1A-1E. The spacer component 140 includes a spacer body 142 and a post engaging member 146 disposed at an end of the spacer body 142. In some embodiments, the spacer component 140 may comprise a single integrally formed component such that the post engaging member 126 is integral to the spacer body 142.

The spacer body 142 may generally comprise a tab or loop. In some embodiments, the spacer body 142 includes an aperture 144 such that one or more other objects can be secured to the spacer body 142. In one example, connective tissue, other tissue, and/or one or more other surgical components may be affixed to the implant 100 by securing the tissue or other components to the spacer body 142 of a spacer component 140 of the implant 100. In addition to serving as an attachment point to the implant 100 for other objects, the spacer component 140 may further be included within the implant to fill at least a portion of the angular range of the center post 110 that is not filled by other components such as staple components 120 or bone plate components 130. One or more spacer components 140 may further be included where desired or necessary to balance lateral forces acting on the locking screw 150 of the implant 100, which may facilitate placement and retention of the implant 100. In the example configuration of FIG. 1E, in which the implant 100 includes a staple component 120 and a bone screw component 130 disposed at an angle of approximately 120°, a spacer component 140 is included at approximately 120° from both the staple component 120 and the bone screw component 130 to balance the lateral forces acting on the locking screw 150. It will be appreciated that one or more bone engagement components, such as staple component 120 and bone screw component 130, and one or more spacer components 140 may be positioned at a variety of radial positions around the center post of the implant 100.

The post engaging member 146 includes a lateral extension 147 sized to seat within the undercut 114 of the aperture 112 of the center post 110 of FIGS. 2A-2E. The post engaging member 146 may further include a curved axial surface 146a and a bevel 146b shaped to conform to complementary contours of the locking screw 150. In various embodiments, any other type of non-vertical surface may be included instead of or in addition to the bevel 146b, to prevent the locking screw 150 and/or any other components from reversing out of the center post 110. Accordingly, seating the post engaging member 146 within the aperture 112 and securing a locking screw 150 within the channel 117 of the center post 110 may rigidly secure the spacer component 140 in a fixed position relative to the center post 110.

FIGS. 9A and 9B depict a locking screw 150 consistent with the implant 100 of FIGS. 1A-1E. The locking screw 150 includes threads 152 and a head 154 including an outward sloping exterior surface 156 and a recess 158 configured to receive a driver. Although the locking screw 150 of FIGS. 9A and 9B includes a hexagonal recess 158, the recess 158 may equally be implemented as a slotted, Phillips, or any other screw drive shape. The threads 152 of the locking screw 150 are angled and pitched to engage with the internal threads 118 of the channel 117 of the center post 110. The exterior surface 156 of the head 154 of the locking screw 150 is disposed at an outward angle corresponding to the angle of the respective bevels 126b, 136b, 146b of the staple component 120, bone plate component 130, and spacer component 140. Accordingly, when all desired staple components 120, bone plate components 130, and/or spacer components 140 of an individual implant 100 have placed, the locking screw 150 can be tightened until it compresses the other components against the interior of the aperture 112 and/or undercut 114 of the center post 100, thereby locking all components of the implant 100 in position.

With reference to FIGS. 10-25, an example internal fixation procedure for placing the implant 100 of FIGS. 1A-1C will be described. Although the procedure of FIGS. 10-25 illustrates placing a particular configuration of the implant 100, it will be understood that the components and steps illustrated and described with reference to FIGS. 10-25 may equally be applied in different sequences and/or with different combinations of components to place the implant 100 in any desired configuration.

Figure 10:
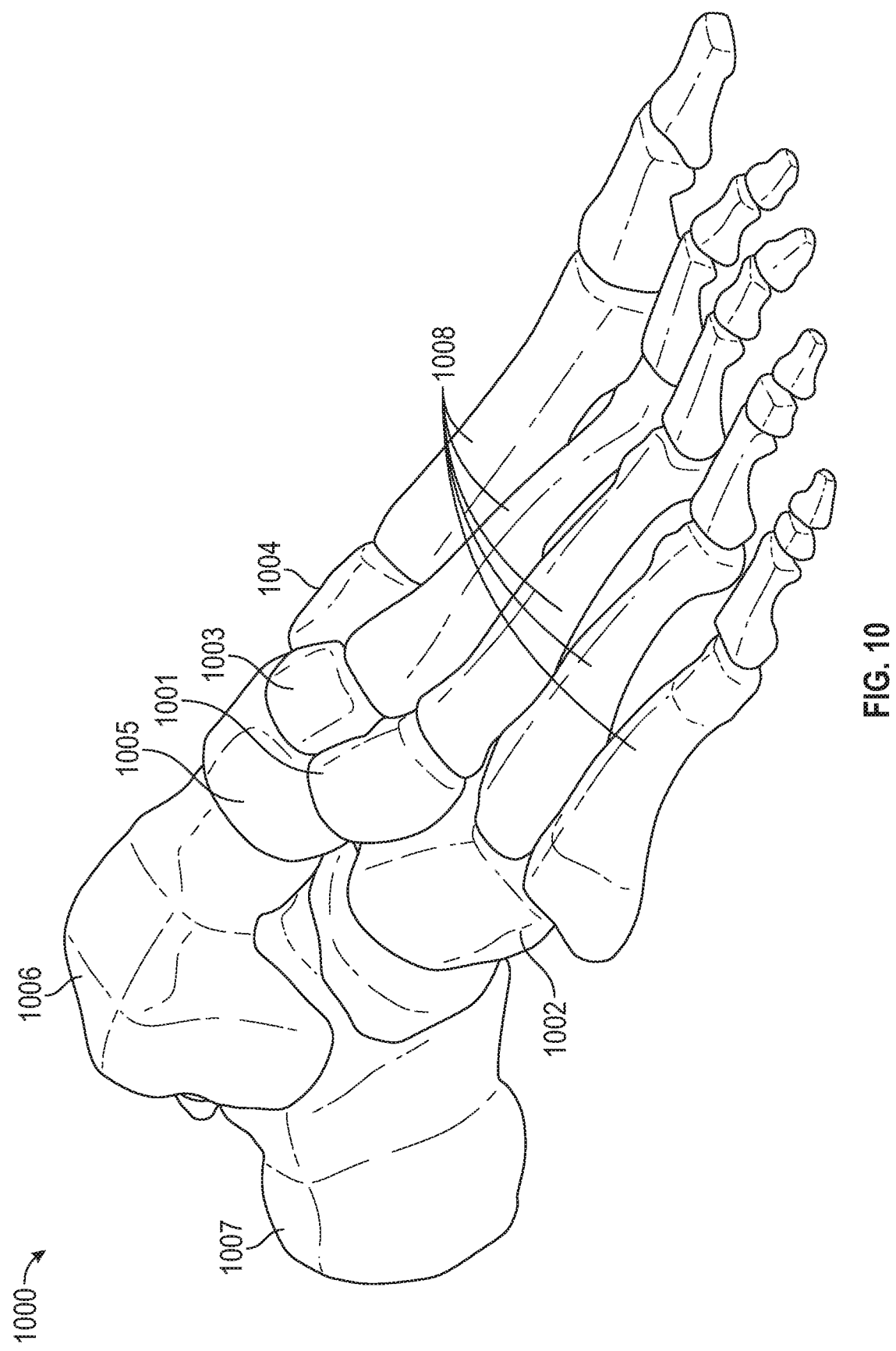
FIGS. 10-25 are perspective views of the bones of a foot, sequentially illustrating an example internal fixation procedure using the example modular bone implant device of FIGS. 1A-1C.

FIG. 10 depicts the bones 1000 of an example human foot prior to placement of the implant 100. In the example procedure of FIGS. 10-25, the implant 100 will be placed to stabilize and join a lateral cuneiform bone 1001 to an adjacent cuboid bone 1002 and intermediate cuneiform bone 1003. However, various other bones of the foot (e.g., other midfoot bones such as a medial cuneiform bone 1004 or navicular bone 1005, hindfoot bones such as a talus bone 1006 or calcaneus bone 1007, metatarsals 1008, etc.) or other bones elsewhere in the body may also be joined with using the implant 100. In some implementations, the modular customizability of the implant 100 may make the implant 100 especially well-suited to locations such as the midfoot, where a plurality of small and/or irregular bones may need to be joined, and where there is a relatively high incidence of skeletal geometry variation between different individual implant placement locations.

Figure 11:
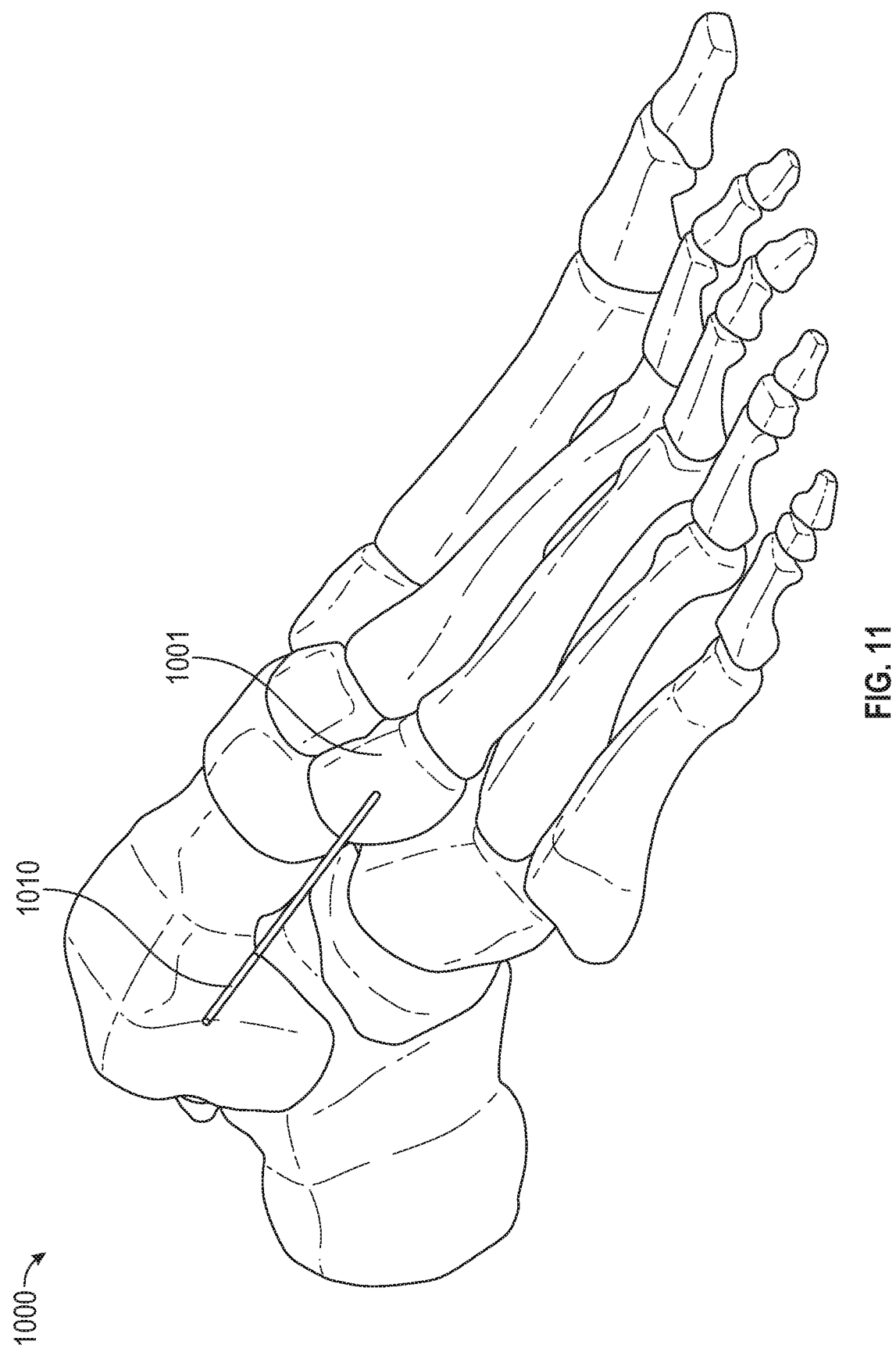

As shown in FIG. 11, the procedure may begin by determining a location for the center post 110. The location and direction of insertion may be marked by the placement of a guide wire 1010 at the location where the center post 110 will be placed. In the example procedure of FIGS. 10-25, the guide wire 1010 is placed into lateral cuneiform bone 1001. The guide wire may be, for example, a Kirschner wire ("K-wire"), or any other suitable type of wire or pin that can be placed into the bone to establish the central axis 101 of the center post 110.

Figure 12:
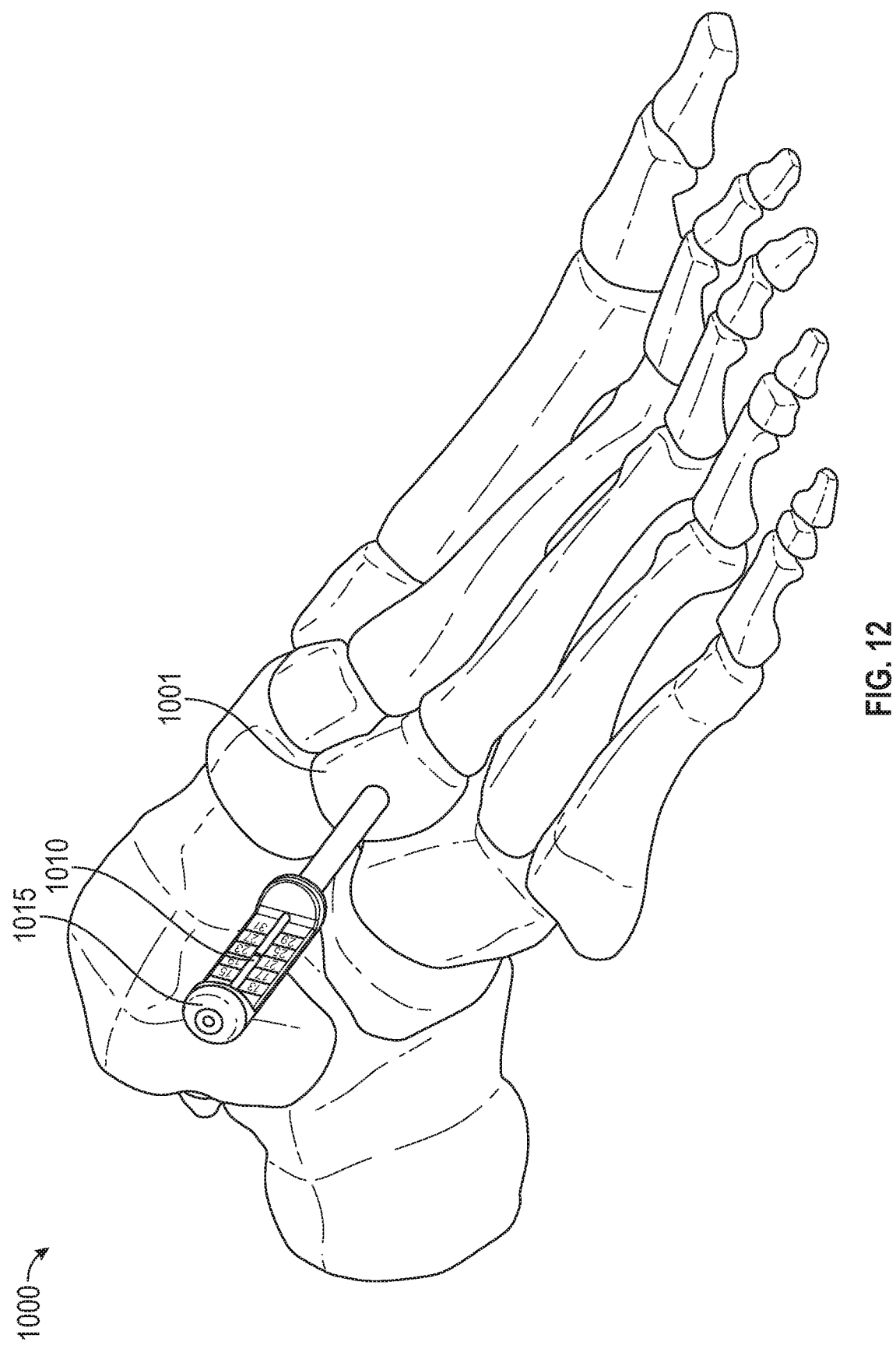
Figure 13:
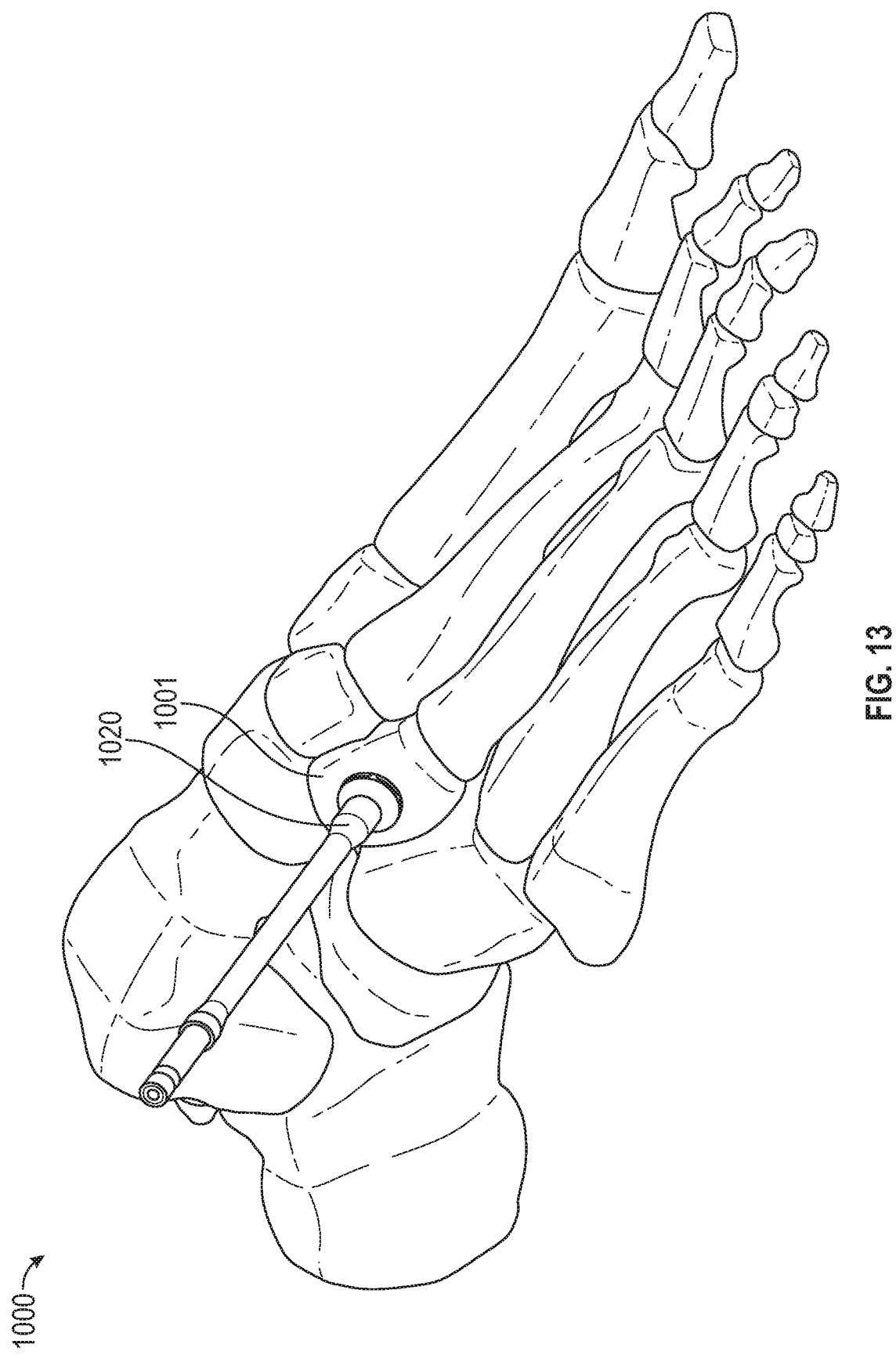

Continuing to FIG. 12, once the guide wire 1010 has been placed, a depth gauge 1015 may be used to determine, with reference to the guide wire 1010, the appropriate depth to drill a pilot hole for the center post 110. The hole may then be drilled as shown in FIG. 13. In some embodiments, the drill may include a drill shaft 1020 and/or drill bit having a cannulated configuration to accommodate the guide wire 1010 while the hole is being drilled.

Figure 14:
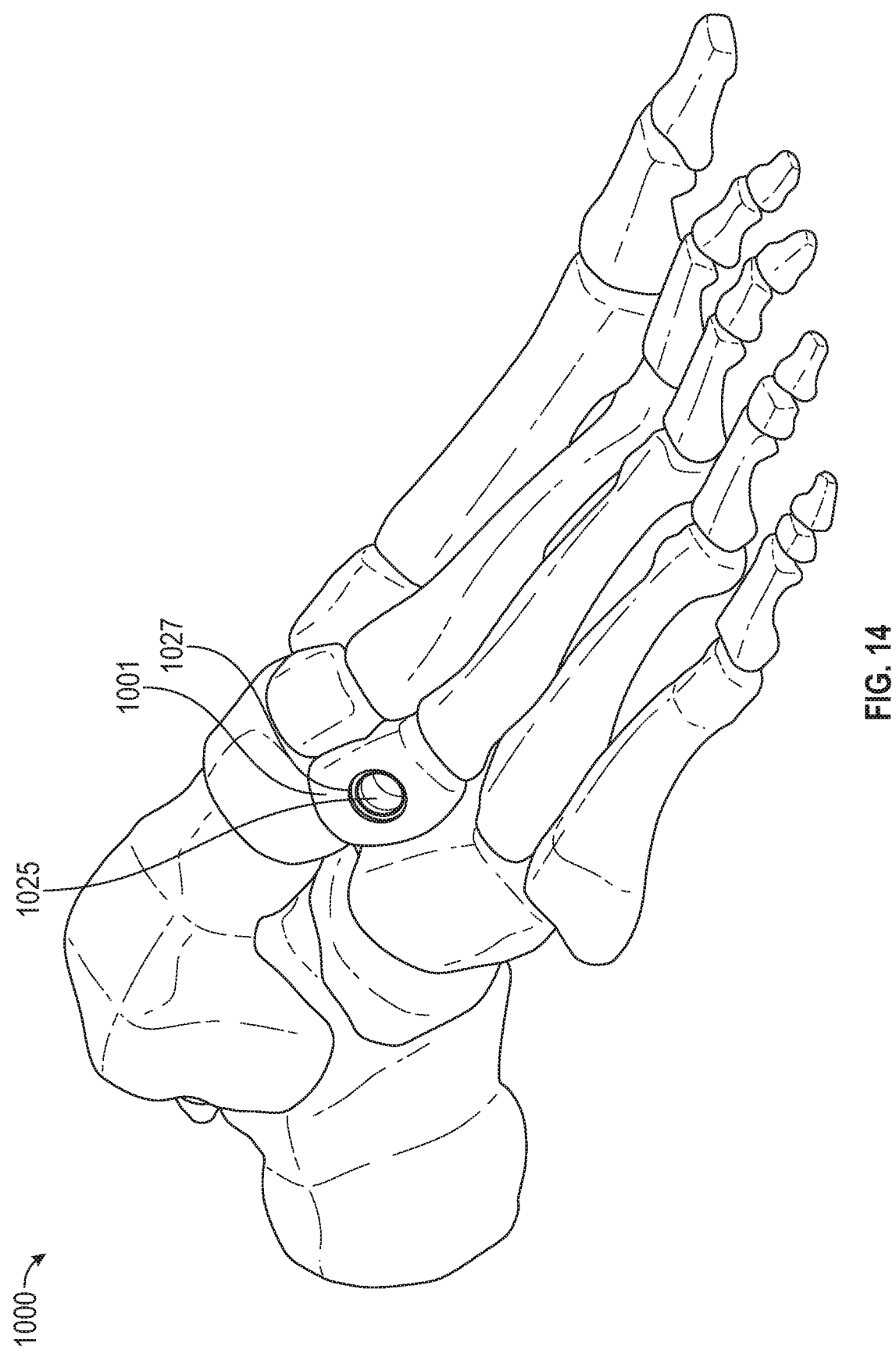

Referring now to FIG. 14, a hole 1025 has been drilled in the lateral cuneiform bone 1001. As shown in FIG. 14, in some embodiments the hole 1025 may include a widened region such as a counterbore 1027 or countersink sized to receive the head 111 of a center post 110 such that the head 111 can lie flush with the exterior surface of the lateral cuneiform bone 1001 when fully inserted.

Figure 15:
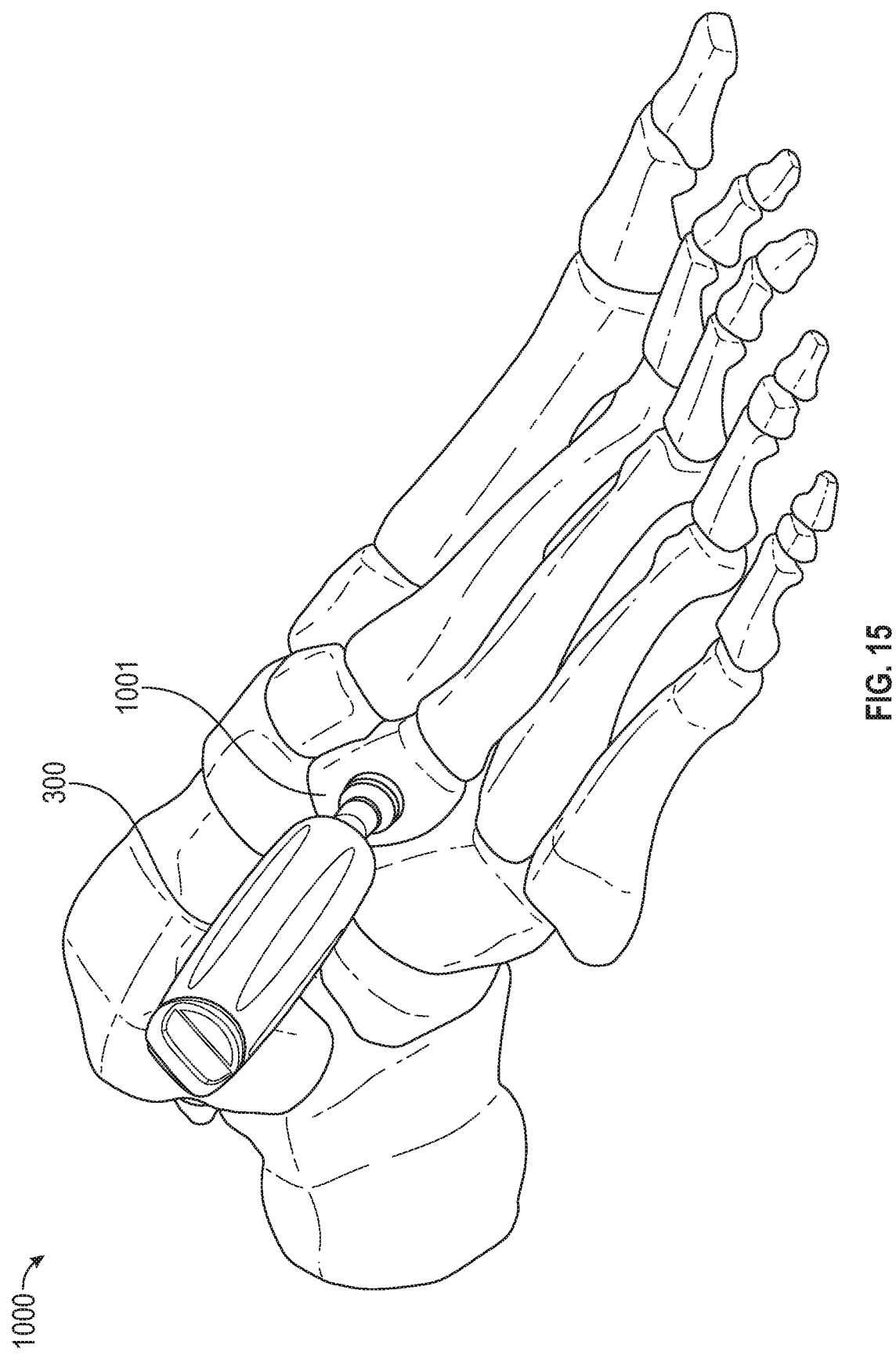
Figure 16:
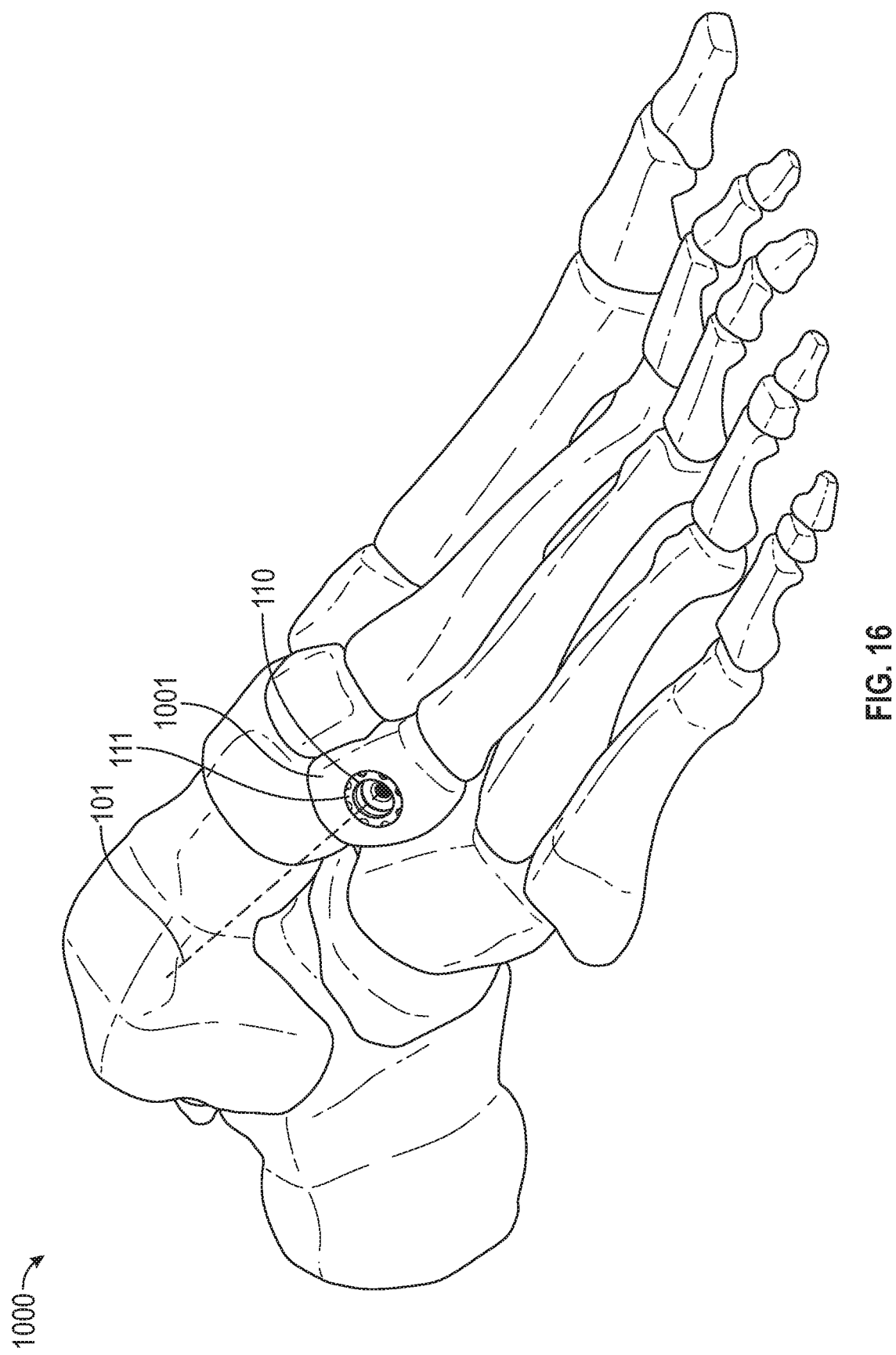

Continuing with reference to FIGS. 15 and 16, a center post 110 may be placed within the hole 1025 using the post driver 300 by a placement method such as the method described herein with reference to FIGS. 2A-3B. In some embodiments, the center post 110 may be one of a plurality of center posts 110 provided within a modular implant kit. The center post 110 may be inserted into the hole 1025 and rotated, using the post driver 300, until the head 111 lies entirely within the hole 1025, for example, within the counterbore 1027. Once the center post 110 has been placed, the bone engagement features 116 of the center post 110 (FIGS. 2A-2E) may anchor the center post 110 in position within the lateral cuneiform bone 1001 to define the central axis 101 of the implant 100.

Figure 17:
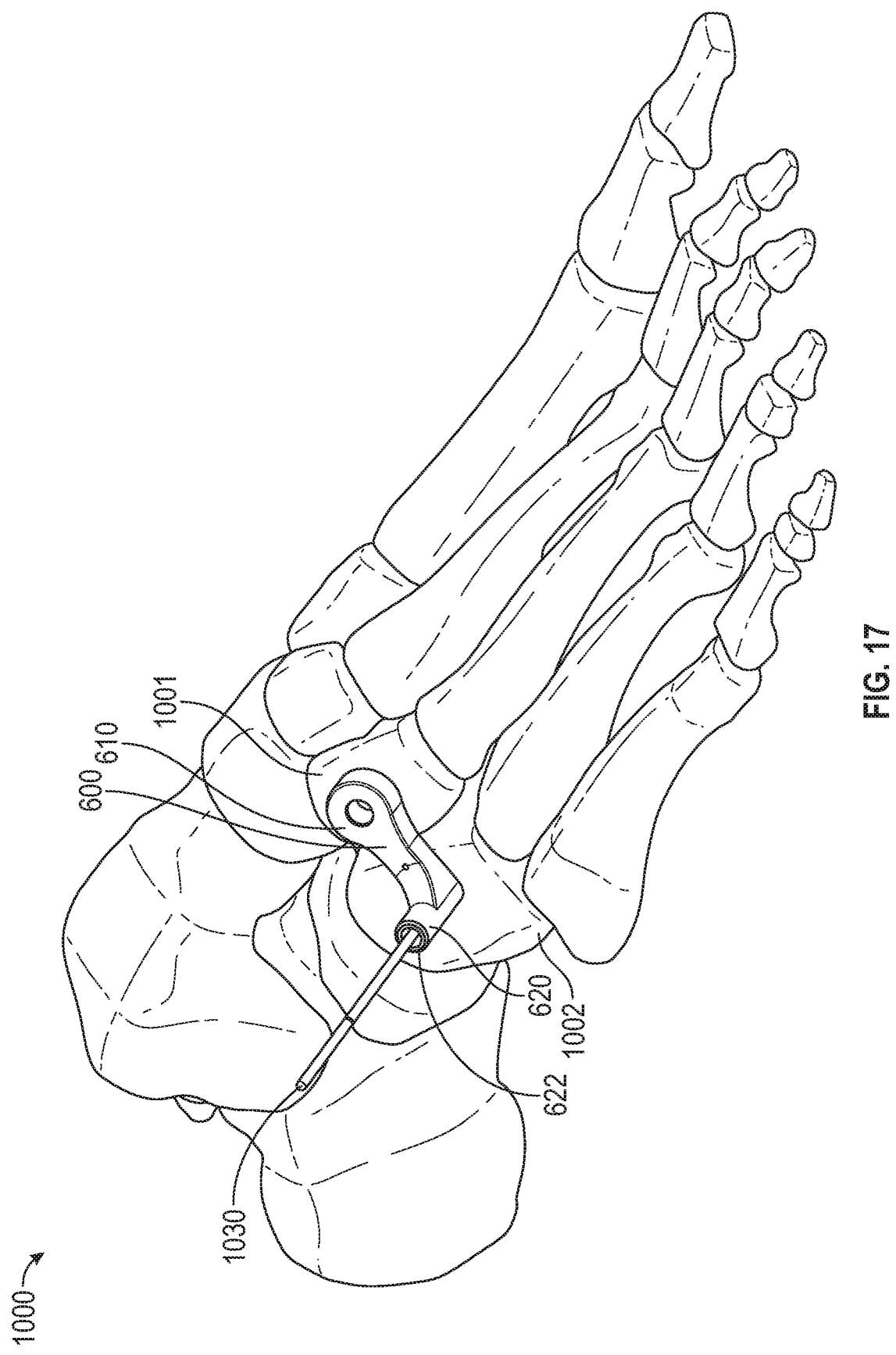

In the example procedure of FIGS. 10-25, the next component to be placed may be a staple component 120 (FIGS. 4A and 4B). In this case, a second hole will be made in a second section of bone to accommodate the bone engaging member 124 of the staple component 120. As shown in FIG. 17, the drill guide 600 of FIGS. 6A-6D is used to select an appropriate location for the second hole. The drill guide 600 is coupled to the center post 110 by snap-fitting the post engaging members 612 of the center post engaging section 610 into the aperture 112 of the center post 110 such that the lateral extensions 614 of the post engaging members 612 seat within the undercut 114 of the aperture 112. When the drill guide 600 is coupled to the center post, the drill guide 600 is rotatable about the central axis 101 such that the drill location section 620 defines a circular set of possible drilling locations. In this example procedure, a location on the cuboid bone 1002 is selected as shown in FIG. 17. In various embodiments, the hole may be drilled through the aperture 622 of the drill location section 620, or the aperture 622 may be used to locate a second guide wire 1030 (e.g., a K-wire or the like) to guide drilling of the hole for the staple component 120.

Figure 18:
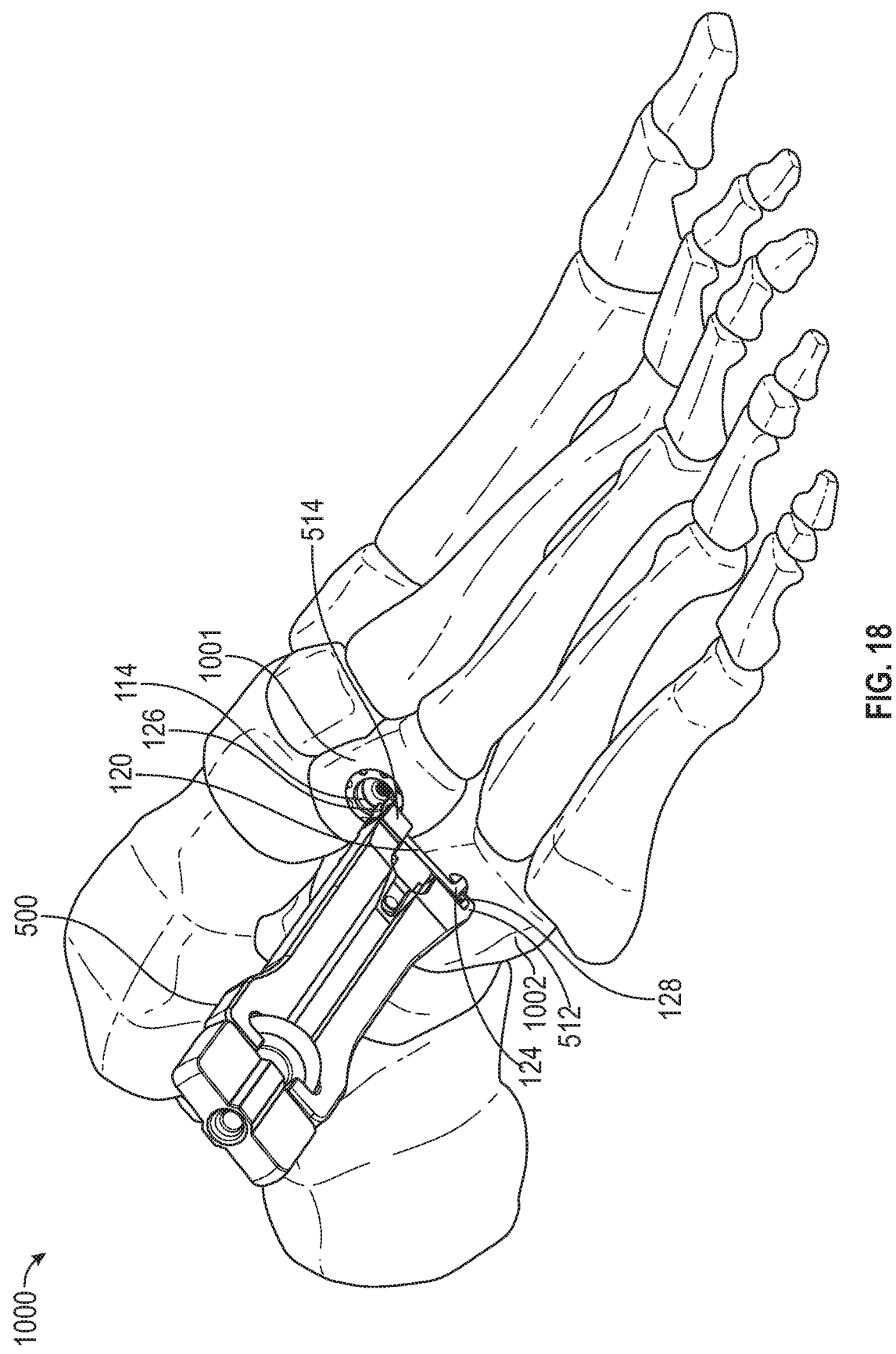
Figure 19:
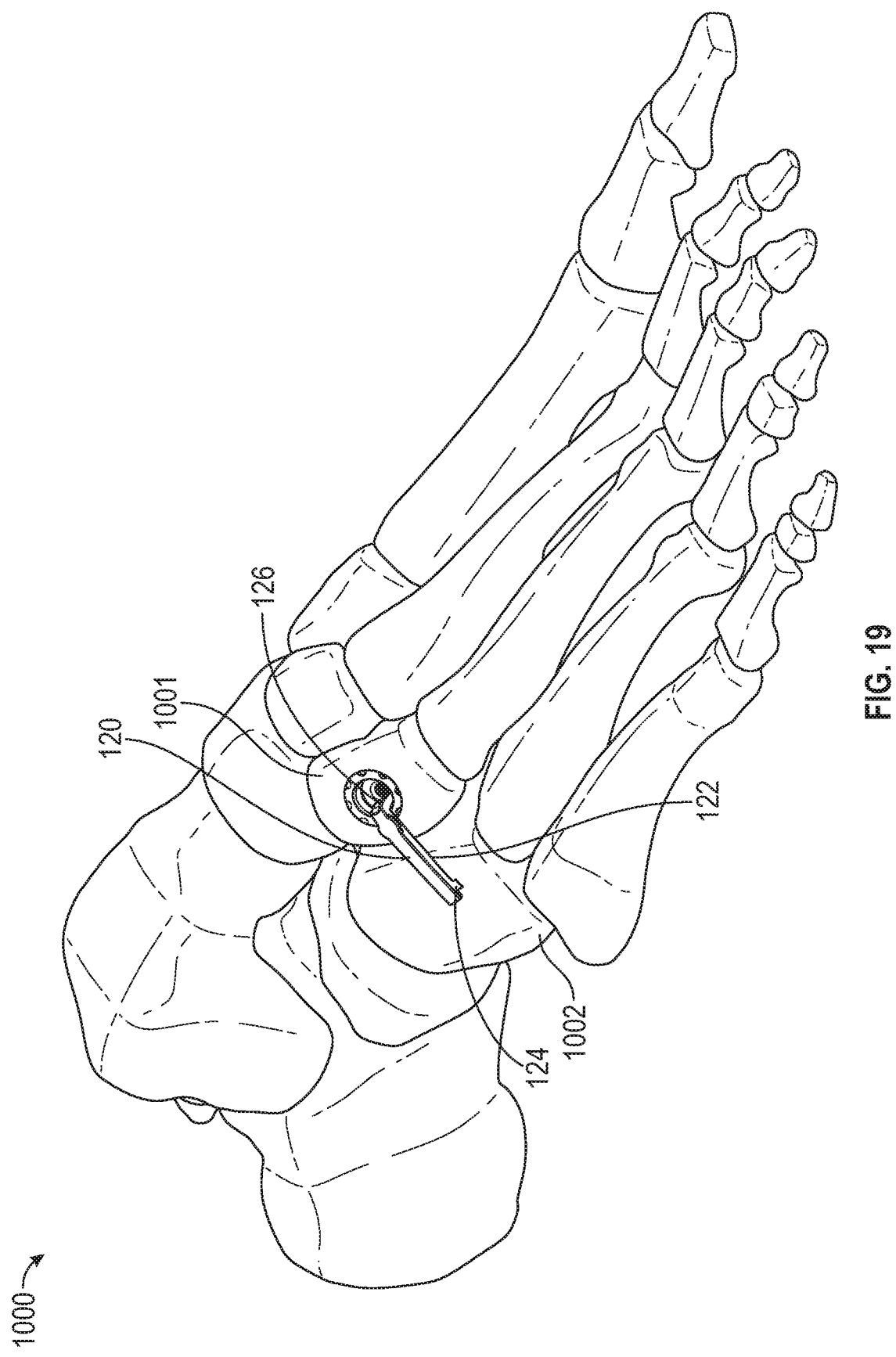

Continuing to FIG. 18, when the second hole has been drilled in the cuboid bone 1002, a staple component 120 may be coupled to the inserter of FIGS. 5A-5D and placed into position. For example, the tip of the bone engaging member 124 may first be placed into the hole in the cuboid bone 1002 and the post engaging member 126 may then be placed into the aperture 112 of the center post 110. When the staple component 120 is fully inserted (e.g., such that an end of the post engaging member 126 abuts a bottom surface of the aperture 112 and/or the lateral extension 127 of the post engaging member 126 sits within the undercut 114), the inserter 500 may be removed from the staple component 120. For example, the plunger adjustment grip 530 may be rotated to release any pressure between the plunger and the bridge 122 of the staple component 120. In some embodiments, rotating the plunger adjustment grip 530 may allow the bridge 122 to return to a more curved configuration, which may further cause the bone engaging features 125 of the bone engaging member 124 to apply force to the interior of the cuboid bone 1002 and thereby create a compressive force between the bone engaging member 124 and the center post 110. The inserter 500 may then be translated radially outward away from the central axis 101, such that the retaining member 512 slides clear of the end extension 128 of the staple component 120 and the retaining members 514 slide clear of the lateral extensions 129 of the staple component 120, to leave the inserted staple component 120 coupled to the center post 110 as shown in FIG. 19. Alternatively, in some embodiments the inserter 500 may be left in place as further steps in the procedure are completed. For example, the inserter 500 may not be removed in some procedures until after the staple component 120 is secured to the center post 110 by the locking screw 150.

Figure 20:
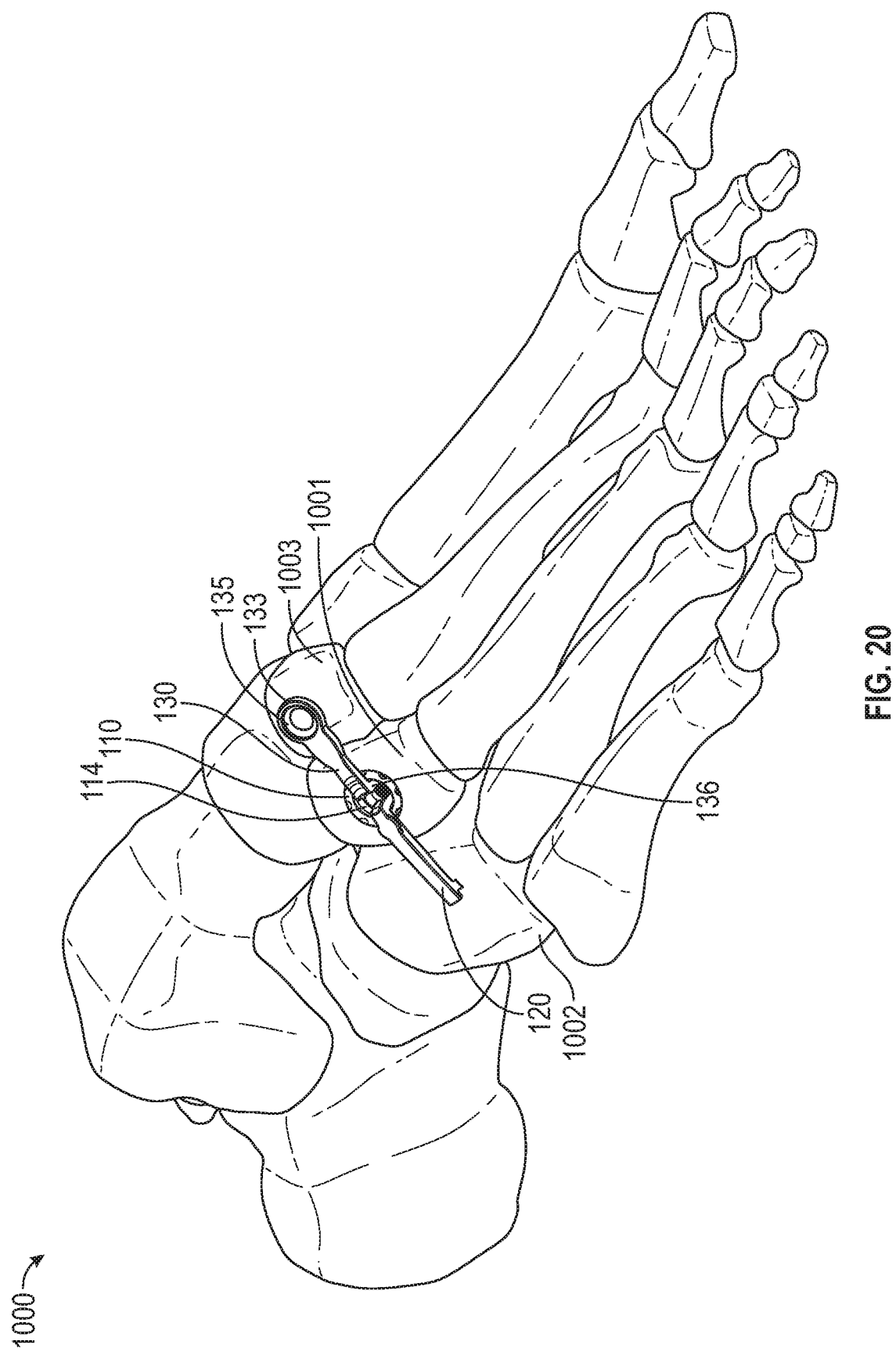
Figure 21:
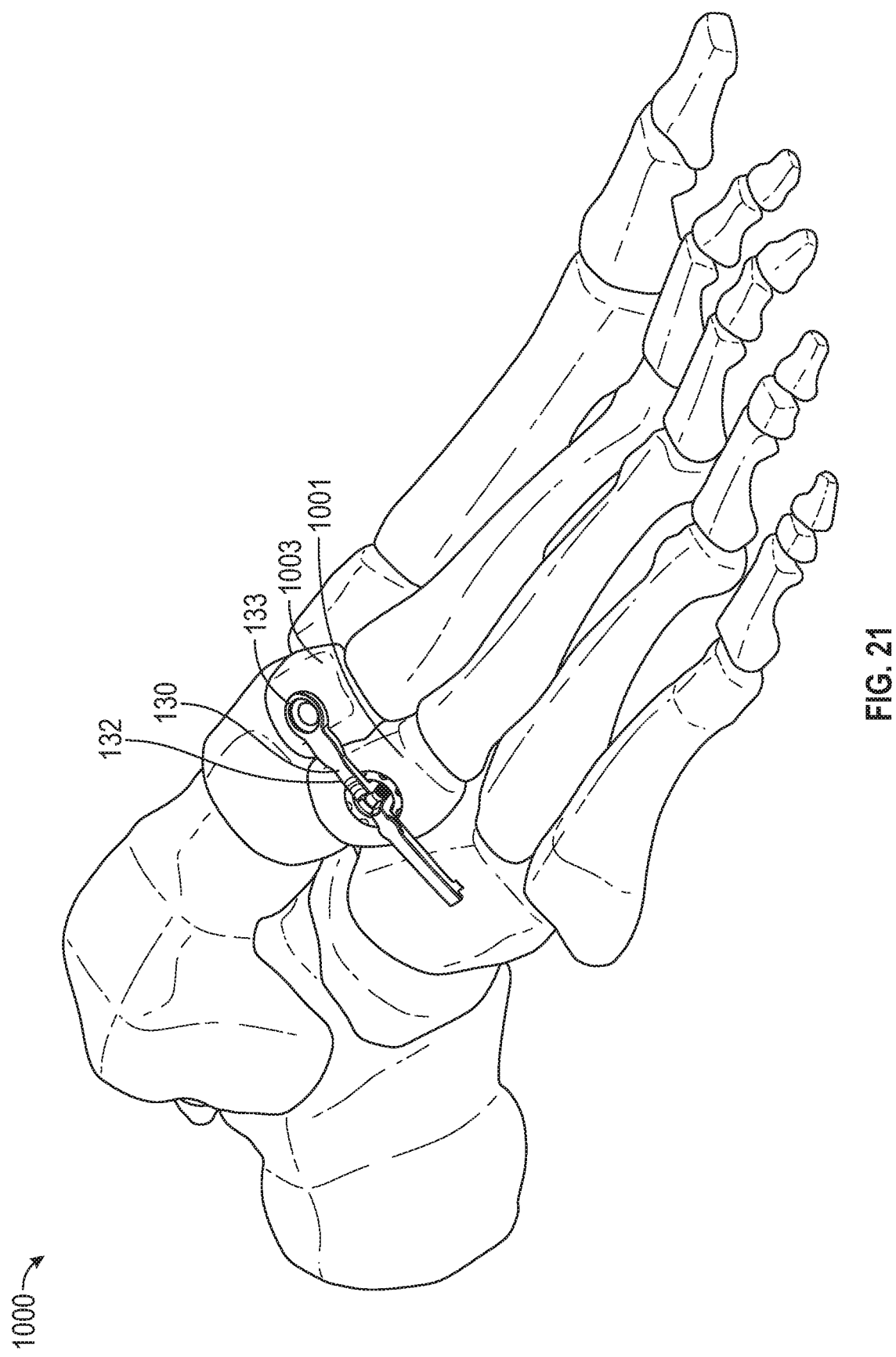
Figure 22:
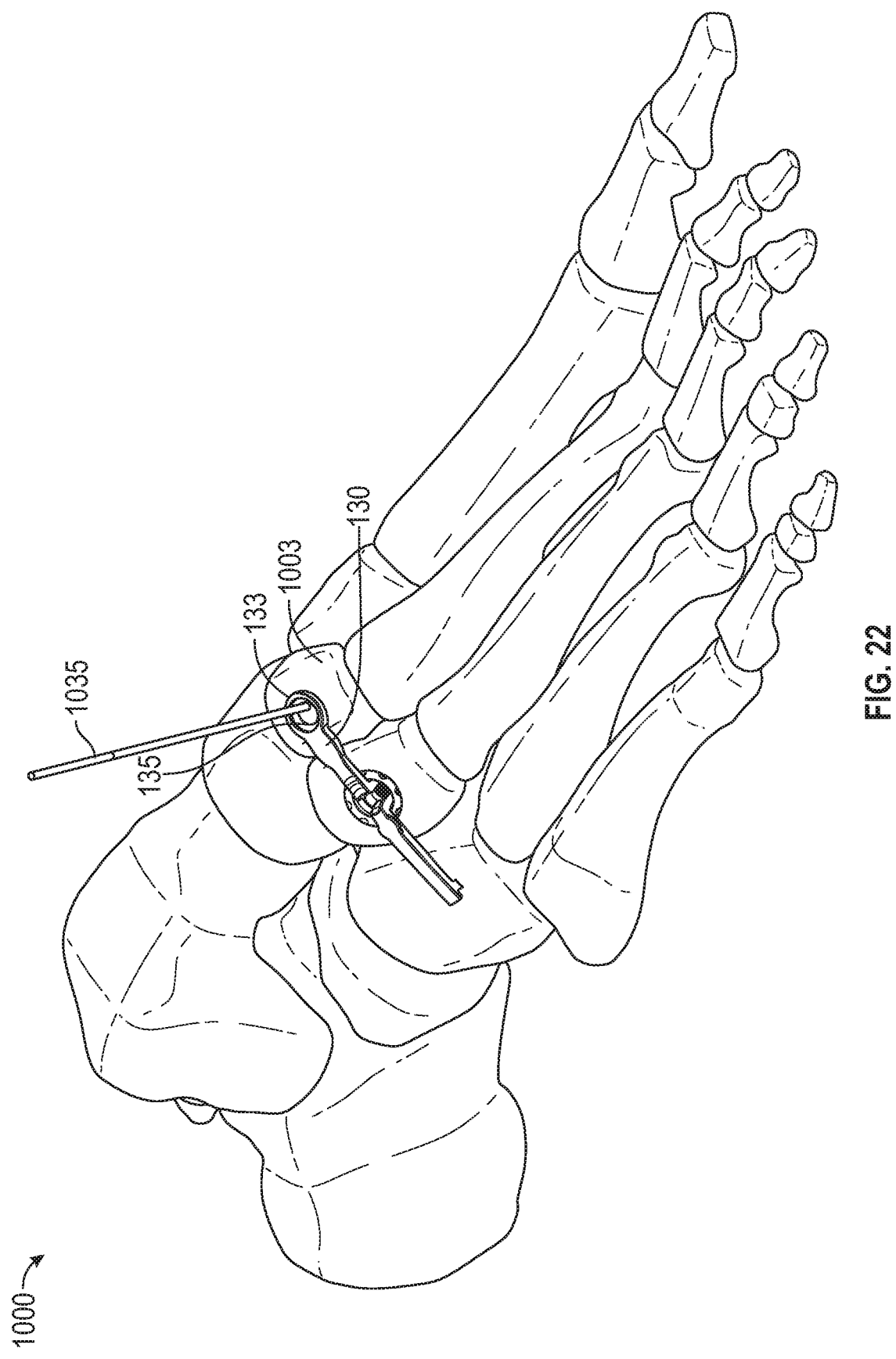

With reference to FIGS. 20-22, a bone plate element 130 may be the next component added to the implant 100. As shown in FIG. 20, an appropriately sized bone plate component 130 may be selected (e.g., if a plurality of different sizes of bone plate components 130 are provided in an implant kit). The bone plate component 130 may be positioned such that the post engaging member 136 of the bone plate component 130 extends into the aperture 112 of the center post 110 and the lateral extension 137 is seated within the undercut 114. The position of the post engaging member 136 along the circumference of the aperture 112 is selected such that the bone screw engaging member 133 is disposed near a desired location for placement of a bone screw 134 (FIGS. 7A-7G). In the example procedure of FIGS. 10-25, the bone screw 134 is to be placed into the intermediate cuneiform bone 1003.

When a bone screw location has been identified, the plate 132 of the bone plate component 130 may be bent, as shown in FIG. 7D, such that at least a portion of the bone screw engaging member 133 abuts the intermediate cuneiform bone 1003. As shown in FIG. 22, a third guide wire 1035 may be placed into the intermediate cuneiform bone 1003 through the aperture 135 of the bone screw engaging member 133. In some embodiments, the third guide wire 1035 may be placed at an outer portion of the aperture 135 such that the guide wire 1035 temporarily holds the bone plate component 130 in place while additional components are positioned. In some embodiments, the third guide wire 1035 may not be used.

Figure 23:
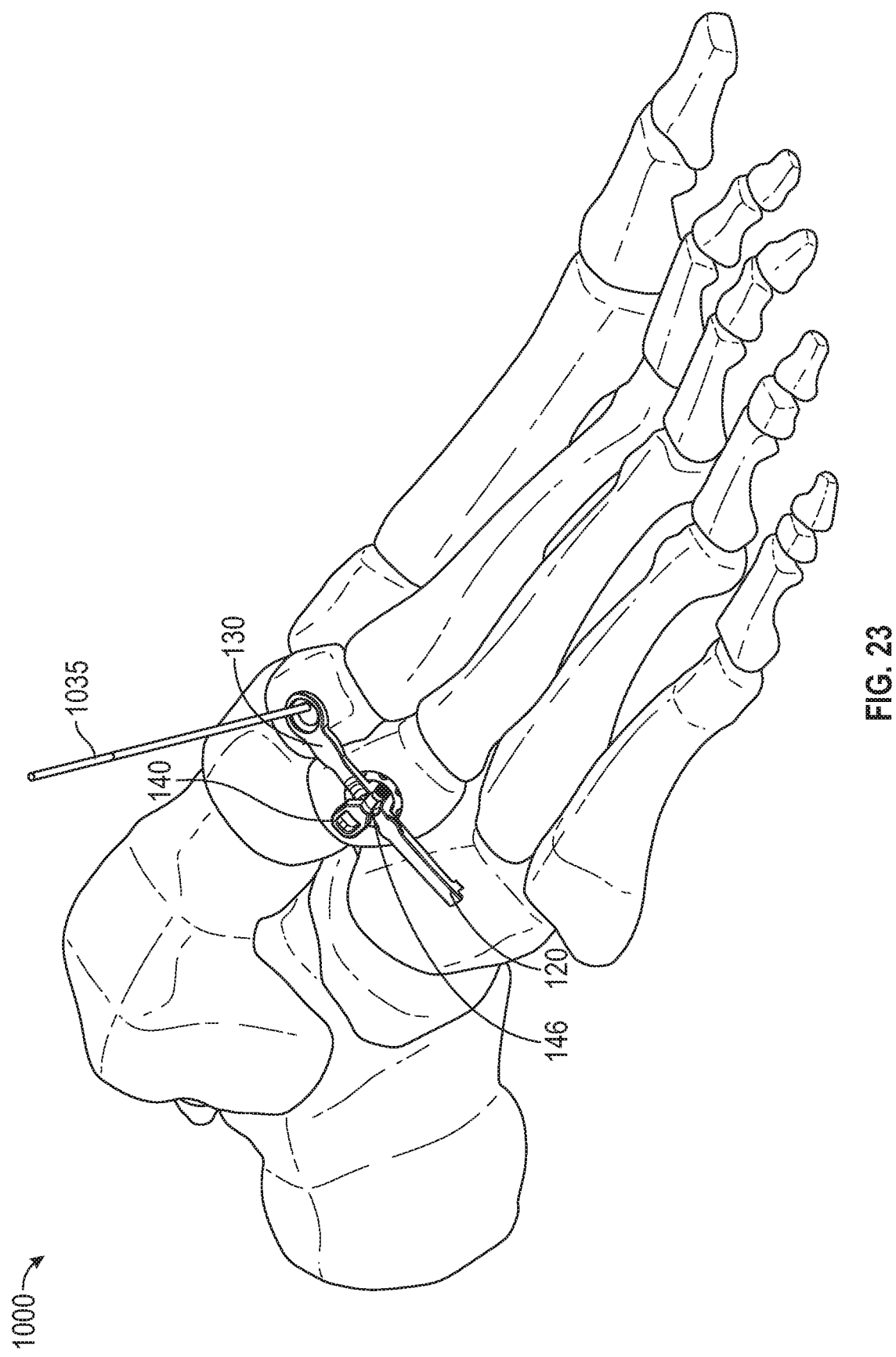

If no additional staple components 120 or bone plate components 130 are to be included in the implant 100, one or more spacer components 14—may then be added if desired. For example, in the procedure of FIGS. 10-25 one spacer component 140 is added at a location angularly disposed between the staple component 120 and the bone plate component 130. As shown in FIG. 23, the post engaging member 146 of the spacer component 140 is placed into the aperture 112 such that the lateral extension 147 is seated within the undercut 114. Because the spacer components 140 do not include a distal portion that engages a bone, it may be desirable to place any spacer components 140 after all staple components 120 and/or bone plate components 130 are placed.

Figure 24:
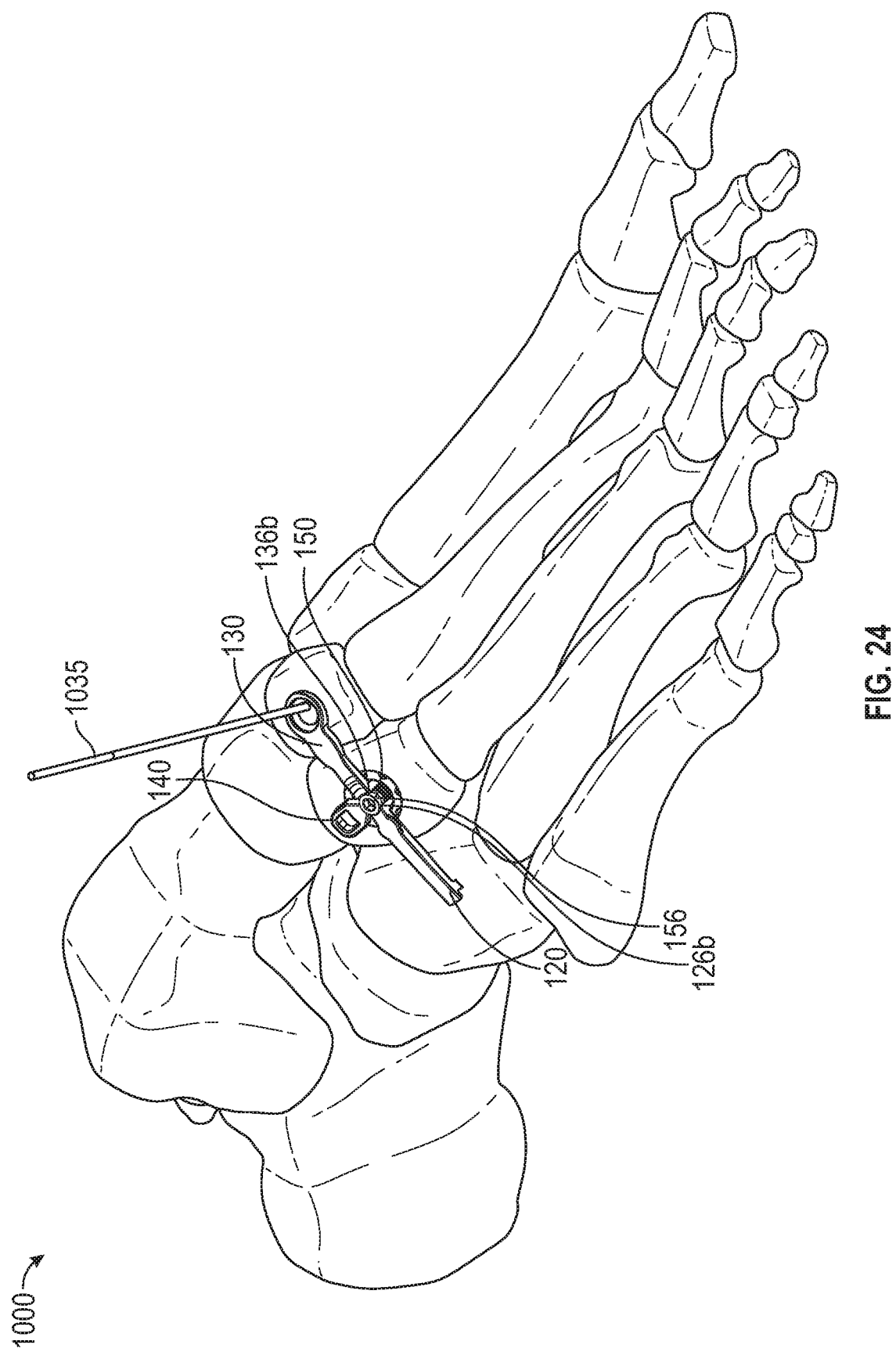

Continuing to the state of FIG. 24, a locking screw 150 may then be provisionally placed within the center post 110. In some embodiments, the locking screw 150 may be rotated using a driver to partially engage the threads 152 of the locking screw 150 with the internal threads 118 of the channel 117 of the center post 110, without driving the locking screw 150 to a fully inserted position. In some implementations, provisional placement of the locking screw 150 may be desirable when one or more bone plate components 130 are included in the implant 100; the presence of the locking screw 150 may generally stabilize the other components, while the less than fully-inserted position of the locking screw 150 may accommodate any slight movement of the post engaging members 136 of the bone plate components 130 as the bone screws 134 are inserted and tightened.

Figure 25:
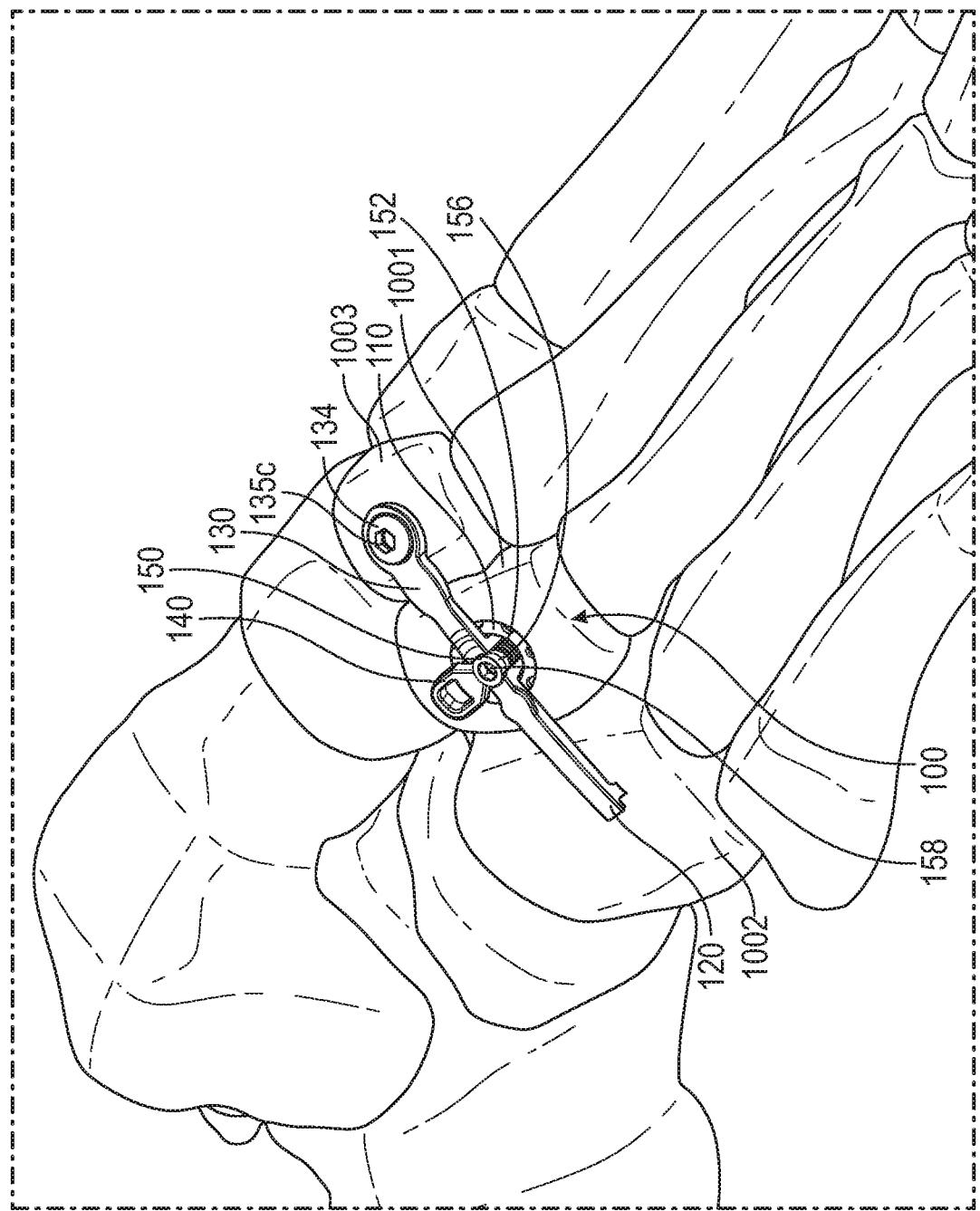

Referring now to FIG. 25, the implant placement procedure of FIGS. 10-25 concludes by inserting a bone screw 134 into the intermediate cuneiform bone 1003 through the aperture 133 of the bone plate component 130 and tightening the locking screw 150 to complete the assembly and placement of the implant 100. In the final assembled state shown in FIG. 25, the locking screw 150 holds the staple component 120, the bone plate component 130, and the spacer component 140 in place. Frictional forces between each post engaging member 126, 136, 146, and the locking screw 150 and/or the inside of the aperture 112, prevent rotation of the staple components 120, bone plate components 130, and/or spacer components 140 about the central axis 101. Accordingly, the example process of FIGS. 10-25 allows the example implant 100 to be assembled in situ within a midfoot or other skeletal location to provide robust internal fixation customized to the unique geometry or other properties of an individual implant location.

The embodiments described herein are exemplary. Modifications, rearrangements, substitute processes, etc. may be made to these embodiments and still be encompassed within the teachings set forth herein. Depending on the embodiment, certain acts, events, or functions of any of the methods described herein can be performed in a different sequence, can be added, merged, or left out altogether (e.g., not all described acts or events are necessary for the practice of the method). Moreover, in certain embodiments, acts or events can be performed concurrently rather than sequentially.

The phrases "connected to," "coupled to," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements, and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y and/or Z). Thus, such disjunctive language is not generally intended to, and should not, imply that certain embodiments require at least one of X, at least one of Y or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A in conjunction with a second processor configured to carry out recitations B and C.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

What is claimed is:

1. A modular bone fixation system comprising:
a center post defining a central axis, the center post having an exterior and an interior, the exterior comprising an outward facing surface, the interior comprising:
an aperture disposed about the central axis on a proximal end of the center post, the aperture configured to receive two or more post engaging members; and
a channel extending along the central axis from the aperture toward a distal end of the center post opposite the proximal end, at least a portion of the channel comprising internal screw threads;
two or more secondary components, each of the two or more secondary components comprising one of:
a bone plate component comprising a plate having a first plate end and a second plate end, the first plate end comprising a first post engaging member configured to engage the aperture of the center post, the second plate end comprising a fastener receiving member configured to receive a fastener therethrough;
a staple component comprising a bridge having a first bridge end and a second bridge end, the first bridge end contiguous with a second post engaging member configured to engage the aperture of the center post, the second bridge end contiguous with a bone engaging member, wherein the staple component is deformable between a first configuration and a second configuration; and
a spacer component comprising a third post engaging member configured to engage the aperture of the center post and a spacer body configured to extend laterally away from the center post when the third post engaging member is disposed within the aperture; and
a locking screw comprising screw threads configured to engage with the internal screw threads of the center post and a head configured to retain the post engaging members of the two or more secondary components within the aperture when the screw threads of the locking screw are engaged with the internal screw threads of the center post.

2. The modular bone fixation implant of claim 1, wherein the aperture of the center post comprises an interlocking feature in a sidewall of the aperture, and wherein the first post engaging member or the second post engaging member comprises a lateral extension configured to seat within the interlocking feature.

3. The modular bone fixation implant of claim 1, wherein the aperture of the center post is a circular aperture and is configured to receive the first or second post engaging member at any of a plurality of angular orientations within the aperture.

4. The modular bone fixation implant of claim 1, wherein at least one of the two or more secondary components is a bone plate component or a staple component.

5. The modular bone fixation implant of claim 1, wherein the spacer body comprises an aperture.

6. The modular bone fixation implant of claim 1, wherein the center post further comprises a plurality of driver engagement features disposed radially about an exterior of the aperture, the driver engagement features configured to receive one or more post head engagement features of a driver such that the driver can exert a rotational force on the center post about the central axis.

7. The modular bone fixation implant of claim 1, wherein the exterior of the center post includes bone engaging features comprising one or more screw threads.

8. The modular bone fixation implant of claim 7, wherein the bone engaging features of the center post are self-tapping screw threads.

9. The modular bone fixation implant of claim 1, wherein the outward facing surface of the center post comprises one or more bone engaging features thereon.

10. The modular bone fixation implant of claim 1, wherein the bone engaging member of the staple component comprises one or more bone engaging features disposed thereon.

11. The modular bone fixation implant of claim 10, wherein the one or more bone engaging features of the staple component comprise ridges oriented to prevent withdrawal of the bone engaging member from a bone.

12. The modular bone fixation implant of claim 1, wherein the fastener is a bone screw.

13. A modular implant kit comprising:
a center post configured to be implanted within bone, wherein the center post defines a central axis of a bone fixation implant; and
a plurality of interchangeable secondary components selected from:
I. one or more staple components comprising a first end configured to be anchored to the center post and a second end configured to engage bone at a location disposed radially outward from the center post;
II. one or more bone plate components comprising a first end configured to be anchored to the center post and a second end configured to receive a bone fastener therethrough to engage bone at a location disposed radially outward from the center post; and
III. one or more spacer components comprising a first end configured to be anchored to the center post; and
a locking screw configured to engage internal screw threads of the center post to lock individual first ends of two or more of the plurality of interchangeable secondary components to the center post simultaneously.

14. The modular implant kit of claim 13, further comprising an inserter configured to facilitate insertion of the one or more staple components.

15. The modular implant kit of claim 13, further comprising a drill guide coupleable to the center post, wherein, when the drill guide is coupled to the center post, the drill guide is rotatable about the central axis to define a plurality of drilling locations for placing the one or more staple components.

16. The modular implant kit of claim 13, further comprising one or more bone screws sized and shaped to couple to the second end of the one or more bone plate components.

17. The modular implant kit of claim 13, further comprising a post driver coupleable to the center post to facilitate application of a rotational force about the central axis to drive the center post into the tissue.

18. The modular implant kit of claim 17, wherein the post driver comprises a longitudinal coupling feature configured to engage the internal screw threads of the center post to longitudinally fix the center post relative to the post driver, and one or more rotational coupling features configured to interlock with a head of the center post to rotationally fix the center post relative to the post driver.

* * * * *